United States Patent [19]

Shuto et al.

[11] Patent Number: 5,684,022
[45] Date of Patent: Nov. 4, 1997

[54] ETHER COMPOUNDS, THEIR USE, AND INTERMEDIATES FOR USE IN THEIR PRODUCTION

[75] Inventors: Akira Shuto, Ashiya; Hirosi Kisida; Toru Tsuchiya, both of Takarazuka; Yoji Takada, Toyonaka; Hiroaki Fujimoto, Funabashi, all of Japan

[73] Assignee: Sumitomo Chemical Company, Limited, Osaka-fu, Japan

[21] Appl. No.: 721,996

[22] PCT Filed: Apr. 6, 1995

[86] PCT No.: PCT/JP95/00664

§ 371 Date: Dec. 12, 1996

§ 102(e) Date: Dec. 12, 1996

[87] PCT Pub. No.: WO95/27700

PCT Pub. Date: Oct. 19, 1995

[30] Foreign Application Priority Data

Apr. 8, 1994 [JP] Japan ..................... 6-070496

[51] Int. Cl.⁶ ............ A01N 43/56; C07D 213/64; C07D 231/12; C07D 231/16; C07D 249/04
[52] U.S. Cl. ............ 514/335; 514/340; 514/341; 514/359; 514/406; 546/261; 546/268.1; 546/275.4; 546/300; 546/302; 548/255; 548/364.1; 548/365.7; 548/375.1; 548/376.1
[58] Field of Search ............ 546/261, 268.1, 546/275.4, 300, 302; 548/255, 364.1, 375.1, 376.1, 365.7; 514/335, 340, 341, 359, 406

[56] References Cited

U.S. PATENT DOCUMENTS

| | | | |
|---|---|---|---|
| 3,640,841 | 2/1972 | Winslow et al. | 162/164.6 |
| 5,071,860 | 12/1991 | Alig et al. | 514/332 |
| 5,102,903 | 4/1992 | Smith | 514/406 |
| 5,116,860 | 5/1992 | Buerstinghaus et al. | 548/376.1 X |
| 5,192,787 | 3/1993 | Bowers et al. | 548/375.1 X |
| 5,315,013 | 5/1994 | Carini et al. | 548/376.1 |
| 5,332,750 | 7/1994 | Mederski et al. | 514/340 |
| 5,374,642 | 12/1994 | Kardorff et al. | 548/365.7 X |
| 5,578,595 | 11/1996 | Boger | 548/376.1 X |

FOREIGN PATENT DOCUMENTS

| | | |
|---|---|---|
| 0 530 702 A1 | 8/1992 | European Pat. Off. |
| 2 008 677 | 9/1971 | Germany |
| 27 45 833 | 4/1979 | Germany |
| 30 25 219 A1 | 1/1982 | Germany |
| 1 330 059 | 9/1973 | United Kingdom |
| 1 592 516 | 7/1981 | United Kingdom |
| 92/14714 | 9/1992 | WIPO |

*Primary Examiner*—Fiona T. Powers
*Attorney, Agent, or Firm*—Birch, Stewart, Kolasch & Birch, LLP

[57] ABSTRACT

There are disclosed novel ether compounds of the general formula:

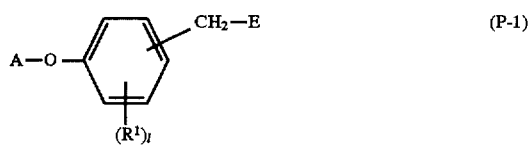

wherein $R^1$ is halogen; A is a group of the general formula Q-1: $-CH(R^2)-(CH_2)_m-CH(R^3)-N(R^4)-C(=Y)-X-R^5$, or the like; E is a group of the general formula:

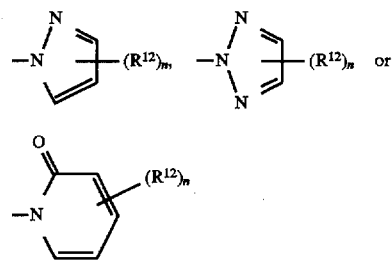

and l is an integer of 0 to 2; harmful-organism controlling agents containing them as active ingredients, and intermediates for use in their production.

11 Claims, No Drawings

ETHER COMPOUNDS, THEIR USE, AND INTERMEDIATES FOR USE IN THEIR PRODUCTION

This application is a 371 of PCT/JP95/00664 filed Apr. 6, 1995.

TECHNICAL FIELD

The present invention relates to ether compounds, their use, and intermediates for use in their production. More particularly, the present invention relates to ether compounds which have excellent controlling effects against harmful organisms, harmful-organism controlling agents containing them as active ingredients, and intermediates for use in the production of these ether compounds.

DISCLOSURE OF THE INVENTION

The present inventors have intensively studied to find compounds which have excellent controlling effects against harmful organisms. As a result, they have found that ether compounds of the general formula P-1 as depicted below have excellent controlling effects against harmful organisms, thereby completing the present invention.

Thus the present invention provides ether compounds (hereinafter referred to as the present compound(s)) of the general formula:

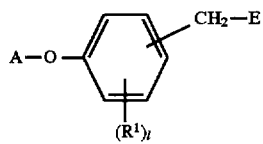
(P-1)

wherein $R^1$ is halogen;

A is any of the groups of the following general formulas Q-1 to Q-11:

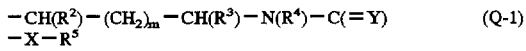 (Q-1)

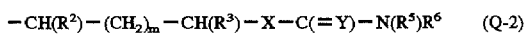 (Q-2)

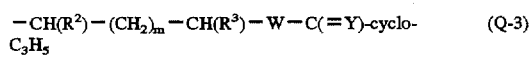 (Q-3)

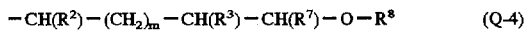 (Q-4)

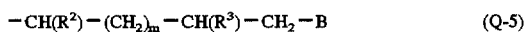 (Q-5)

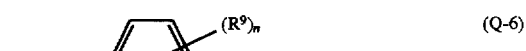 (Q-6)

 (Q-7)

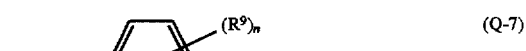 (Q-8)

 (Q-9)

-continued

A is any of the groups of the following general formulas Q-1 to Q-11:

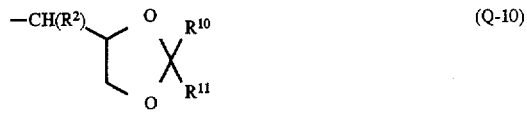 (Q-10)

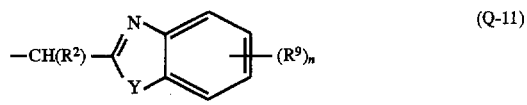 (Q-11)

$R^2$, $R^3$, $R^4$ and $R^7$ are independently hydrogen or methyl;

$R^5$ and $R^8$ are independently $C_1$–$C_4$ alkyl (optionally substituted with halogen or methoxy), $C_3$–$C_4$ alkenyl (optionally substituted with halogen) or $C_3$–$C_4$ alkynyl (optionally substituted with halogen);

$R^6$ is a group represented by $R^5$, or hydrogen;

$R^9$ is halogen or $C_1$–$C_4$ alkyl (optionally substituted with halogen);

$R^{10}$ and $R^{11}$ are independently hydrogen, $C_1$–$C_4$ alkyl or $C_3$–$C_4$ alkenyl;

B is a group of the general formula:

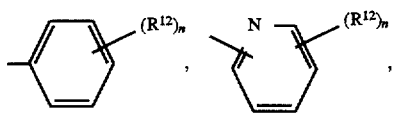

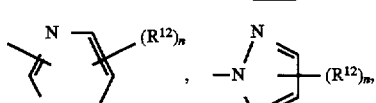

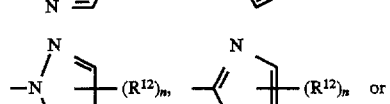

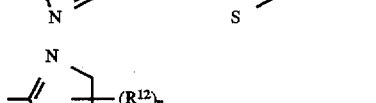

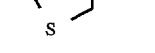

E is a group of the general formula:

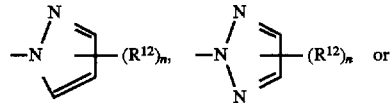

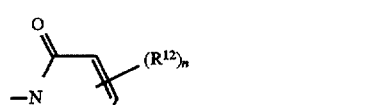

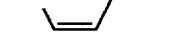

$R^{12}$ is halogen, or methyl optionally substituted with halogen;

X and Y are independently oxygen or sulfur;

W is oxygen, sulfur or NH; and l, m and n are independently an integer of 0 to 2; and harmful-organism controlling agents containing them as active ingredients.

The present invention further provides a phenol compound of the general formula:

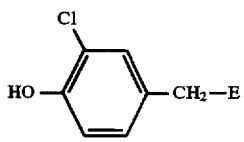
(P-2)

wherein E is as defined above, which is useful as an intermediate for use in the production of the above ether compound.

The present compounds have excellent juvenile hormone-like activity particularly against insects, i.e., they have functions such as inhibition of metamorphosis into adults, inhibition of embryogenesis and sterilization of adults. For this reason, the present compounds may serve generally as growth regulators, chemosterilants, ovicides or reproduction inhibitors to produce high controlling effects against various noxious insects, including those having an increased resistance to the existing insecticides, such as those which are found in agriculture, forestry and horticulture; those which infest stored grains; and those which are detrimental to health.

EMBODIMENTS FOR MAKING THE INVENTION

The present compounds are represented by the above general formula P-1.

As the halogen represented by $R^1$, $R^9$ and $R^{12}$, there can be mentioned fluorine, chlorine, bromine or iodine.

As the $C_1$–$C_4$ alkyl (optionally substituted with halogen or methoxy group) represented by $R^5$, $R^6$ and $R^8$, there can be mentioned, for example, methyl, ethyl, n-propyl, isopropyl, n-butyl, isobutyl, sec-butyl, 2,2,2-trifluoroethyl, 2-fluoroethyl, 2-chloroethyl, 2-bromoethyl, 2,2,3,3,3-pentafluoropropyl, methoxyethyl and 3-methoxypropyl.

As the $C_3$–$C_4$ alkenyl (optionally substituted with halogen) represented by $R^5$, $R^6$ and $R^8$, there can be mentioned, for example, allyl, 2-methylallyl, 2-butenyl, 1-methylallyl, 2-chloroallyl and 3,3-dichloroallyl.

As the $C_3$–$C_4$ alkynyl (optionally substituted with halogen) represented by $R^5$, $R^6$ and $R^8$, there can be mentioned, for example, propargyl, 2-butynyl, 4,4,4-trifluoro-2-butynyl.

As the $C_1$–$C_4$ alkyl (optionally substituted with halogen) represented by $R^9$, there can be mentioned, for example, methyl, ethyl, n-propyl, isopropyl, sec-butyl, isobutyl, tert-butyl, trifluoromethyl and 2,2,2-trifluoroethyl.

As the $C_1$–$C_4$ alkyl represented by $R^{10}$ and $R^{11}$, there can be mentioned, for example, methyl, ethyl, propyl, 2-methylethyl, butyl, 2-methylpropyl, 1-methylpropyl or 1,1-dimethylethyl.

As the $C_3$–$C_4$ alkenyl represented by $R^{10}$ and $R^{11}$, there can be mentioned, for example, allyl, 2-butenyl, 2-methylallyl or 1-methylallyl.

As the methyl optionally substituted with halogen, which is represented by $R^{12}$, there can be mentioned, for example, methyl, difluoromethyl and trifluoromethyl.

In the present compounds, the position for substitution of $CH_2$-E- is preferably p- or m-position with respect to A-O-, particularly preferred being p-position.

In the present compounds, E is preferably a group of the general formula:

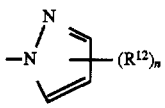
(P-3)

wherein $R^{12}$ and n are as defined above, among which particularly preferred is a group where n is 0.

A is preferably one of the groups represented by Q-1, Q-2, Q-3, Q-5 and Q-10, among which preferred is a group where $R^2$, $R^3$ and $R^4$ are all hydrogen, and m is preferably 0. As the particularly preferred A, there can be mentioned a group represented by Q-1. B is preferably a group of the general formula P-3.

When the present compounds have an asymmetric carbon atom(s), their both optically active isomers (i.e., (+)- and (–)-forms) having biological activity, and mixtures thereof at any ratio, are included in the present invention.

The present compounds can be produced, for example, by reacting a phenol derivative of the general formula:

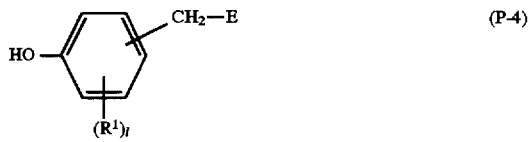
(P-4)

wherein $R^1$, E and l are as defined above, with a compound of the general formula:

A-L      (P-5)

wherein A is as defined above and L is halogen (e.g., chlorine, bromine, iodine), mesyloxy or tosyloxy, in the presence of a base.

This reaction is usually effected in an inert organic solvent. As the solvent which can be used, there can be mentioned, for example, aromatic hydrocarbons such as benzene, toluene, xylene and chlorobenzene; nitriles such as acetonitrile, propionitrile and isobutyronitrile; ketones such as acetone, methyl isobutyl ketone and methyl ethyl ketone; alcohols such as methanol, ethanol and n-propyl alcohol; ethers such as diethyl ether, diisopropyl ether, 1,2-diethoxyethane, tetrahydrofuran and dioxane; polar solvents such as N,N-dimethylformamide, N,N-dimethylacetamide, dimethylsulfoxide, sulforane and hexamethylphosphoric triamide; water; or mixtures thereof. To make more smooth progress in the reaction, phase transfer catalysts may be added, such as benzyltriethyl-ammonium chloride and tetra-n-butylammonium bromide.

As the base which can be used, there can be mentioned, for example, alkali metals such as sodium and potassium; alkali metal hydroxides such as sodium hydroxide and potassium hydroxide; alkali metal carbonates such as sodium carbonate and potassium carbonate; alkali metal hydrides such as sodium hydride; metal alkoxides such as sodium ethoxide and sodium methoxide; and organic bases such as pyridine, triethylamine, N,N-dimethylaniline and 4-N,N-dimethylaminopyridine.

The reaction is usually effected in the range of 0° C. to 200° C. or the boiling point of the solvent used, preferably in the range of 20° C. to 120° C. The reaction time is usually 1 to 50 hours.

The amounts of reagents to be used in the reaction are usually in the ratio of from 1 to 10 moles, preferably from 1 to 2 moles, for each of the compound of the general formula P-5 and the base, to 1 mole of the phenol derivative of the general formula P-4.

After completion of the reaction, the reaction mixture, after neutralized, if necessary, by addition of an aqueous ammonium chloride solution, is subjected to ordinary post-treatments such as extraction with an organic solvent and concentration to isolate the present compounds. If necessary, purification may be carried out by silica gel chromatography or recrystallization.

The present compounds can be produced according to the following reaction scheme 1, 2, 3 or 4:

Reaction Scheme 1

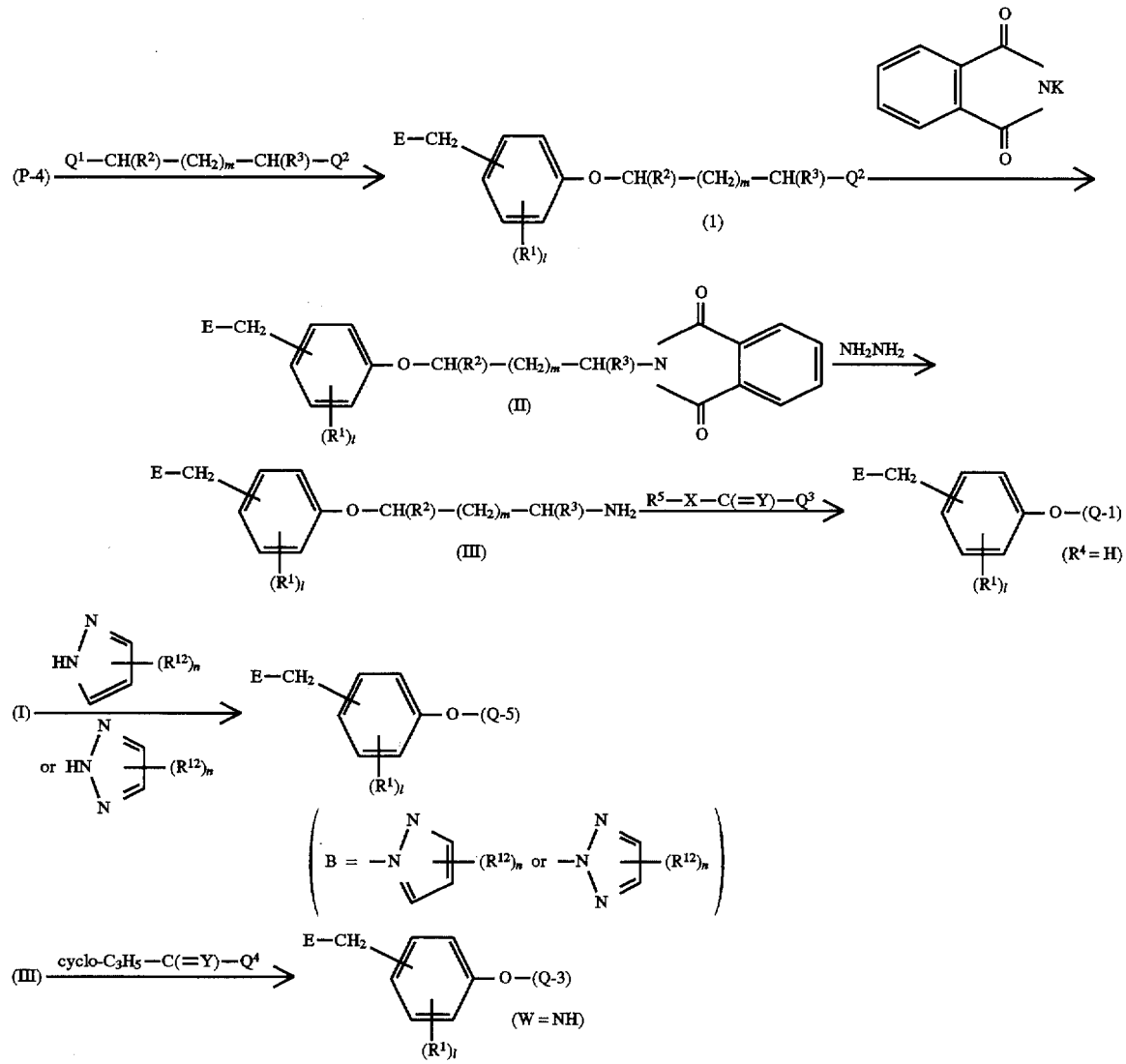

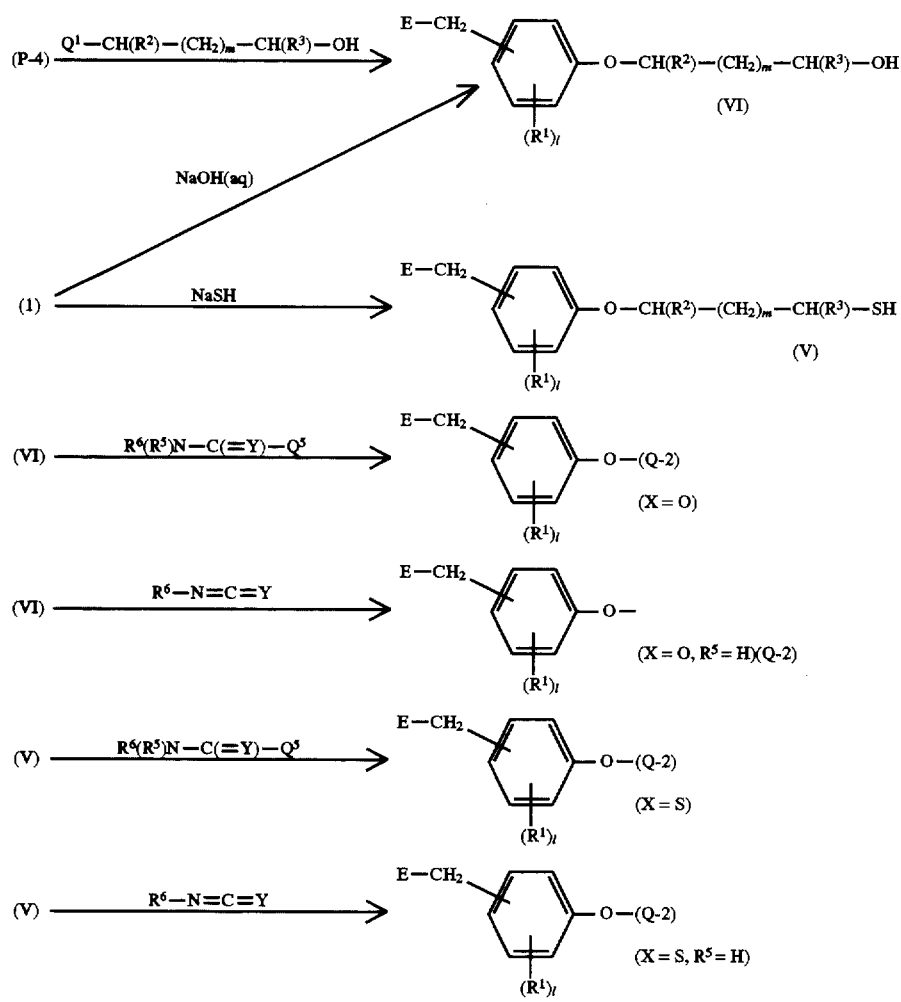
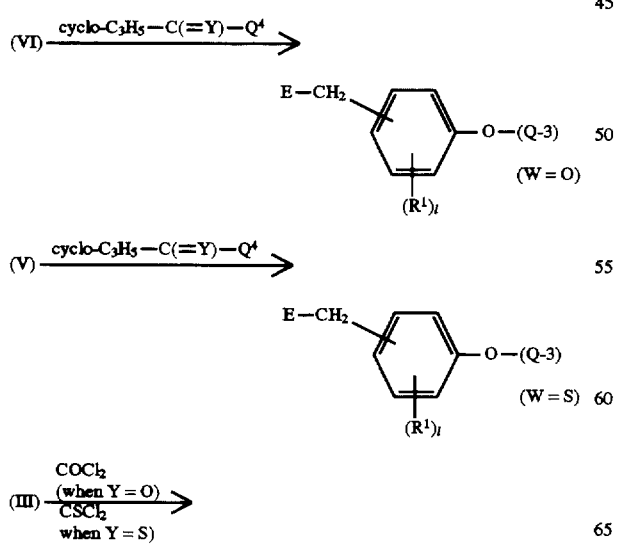
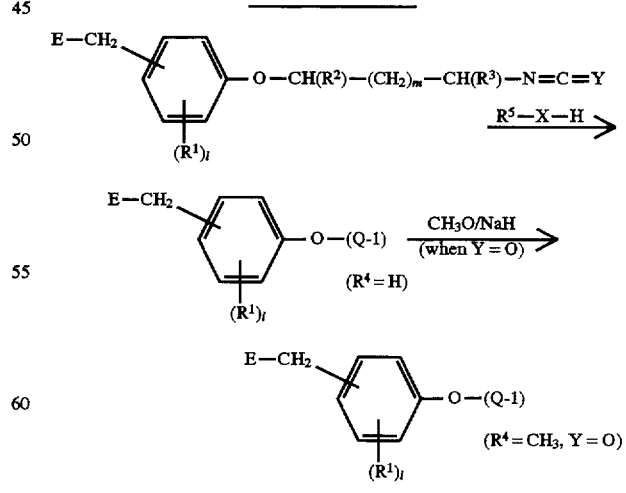

Reaction Scheme 3 (continued)

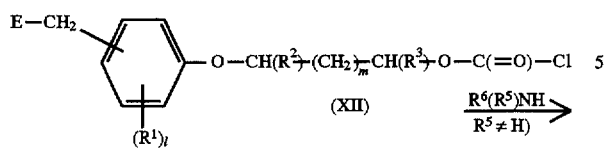

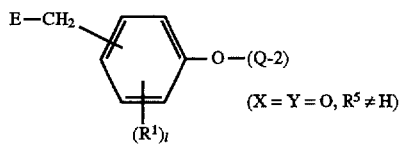

(continued)

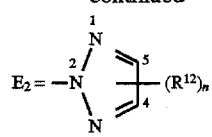

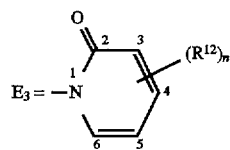

Reaction Scheme 4

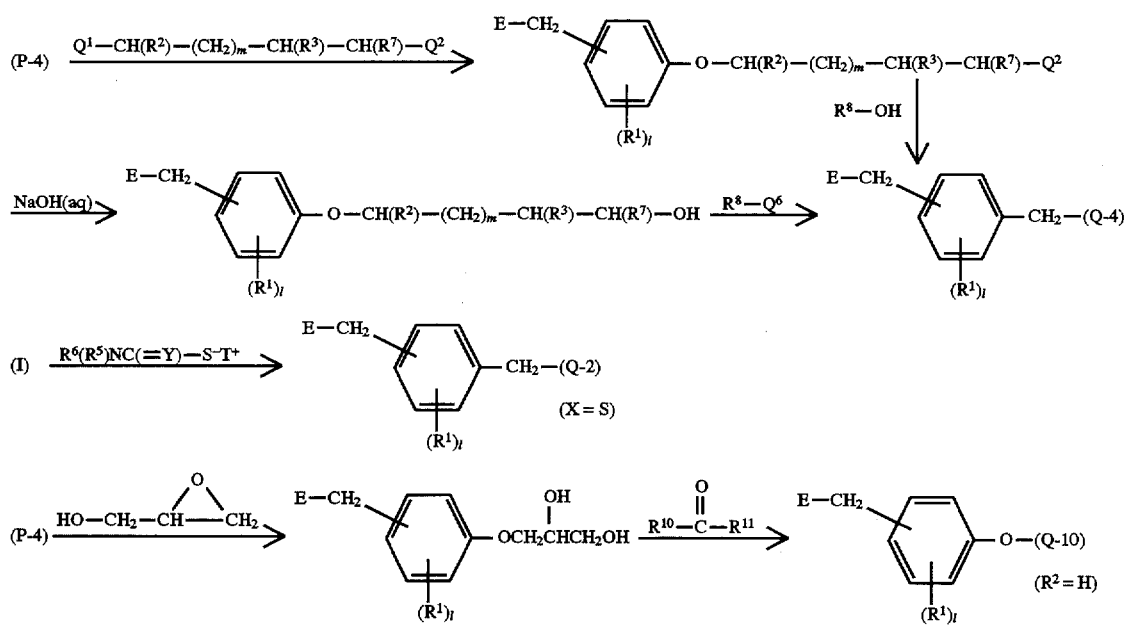

In the above reaction schemes 1, 2, 3 and 4, $R^2$, $R^3$, $R^4$, $R^5$, $R^6$, $R^7$, $R^8$, X, Y, l and m are as defined above; $Q^1$, $Q^2$, $Q^3$, $Q^4$ and $Q^5$ are halogen (e.g., chlorine, bromine, iodine); and T is an alkali metal (e.g., sodium, potassium), a quaternary ammonium salt or $NH_2(R^5)R^6$.

Tables 1 to 13 below show some typical examples of the present compounds of the general formula:

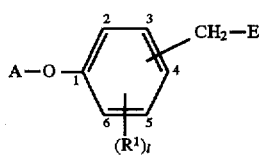

wherein E is any of $E_1$, $E_2$ or $E_3$ as depicted below:

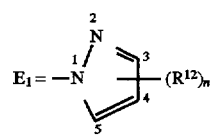

TABLE 1

| A | $(R^1)_l$ | Position for substitution of $CH_2$—E | E | $(R^{12})_n$ |
|---|---|---|---|---|
| $CH_2CH_2NHCO_2CH_3$ | H | 4 | $E_1$ | H |
| $CH_2CH_2NHCO_2C_2H_5$ | H | 4 | $E_1$ | H |
| $CH_2CH_2NHCO_2C_2H_5$ | H | 4 | $E_1$ | 3-$CH_3$ |
| $CH_2CH_2NHCO_2C_2H_5$ | H | 4 | $E_1$ | 5-$CH_3$ |
| $CH_2CH_2NHCO_2C_2H_5$ | H | 3 | $E_1$ | H |
| $CH_2CH_2NHCO_2CH_3$ | H | 4 | $E_2$ | H |
| $CH_2CH_2NHCO_2C_2H_5$ | H | 4 | $E_2$ | H |
| $CH_2CH_2NHCO_2C_2H_5$ | H | 3 | $E_2$ | H |
| $CH_2CH_2NHCO_2CH_3$ | H | 3 | $E_2$ | H |
| $CH_2CH_2NHCO_2C_2H_5$ | H | 3 | $E_1$ | 3,5-$(CH_3)_2$ |
| $CH_2CH_2NHCO_2C_2H_5$ | H | 4 | $E_1$ | 3,5-$(CH_3)_2$ |
| $CH_2CH_2NHCO_2C_2H_5$ | H | 4 | $E_1$ | 4-Cl |
| $CH_2CH_2NHCO_2CH_3$ | H | 3 | $E_1$ | H |
| $CH_2CH_2NHCO_2CH_3$ | H | 3 | $E_1$ | 3-$CH_3$ |
| $CH_2CH_2NHCO_2CH_3$ | H | 3 | $E_1$ | 5-$CH_3$ |
| $CH_2CH_2NHCO_2C_2H_5$ | H | 4 | $E_1$ | 4-Br |
| $CH_2CH_2NHCO_2C_2H_5$ | H | 3 | $E_1$ | 4-I |
| $CH_2CH_2NHCO_2C_2H_5$ | 2-Cl | 4 | $E_1$ | H |
| $CH_2CH_2NHCO_2C_2H_5$ | 2-F | 4 | $E_1$ | H |
| $CH_2CH_2NHCO_2CH_3$ | 2-Cl | 4 | $E_1$ | H |

TABLE 1-continued

| A | $(R^1)_1$ | Position for substitution of $CH_2$—E | E | $(R^{12})_n$ |
|---|---|---|---|---|
| $CH_2CH_2NHCO_2C_2H_5$ | 2,5-$Cl_2$ | 4 | $E_1$ | H |
| $CH_2CH_2NHCO_2C_2H_5$ | 2-Cl | 4 | $E_1$ | 3-$CH_3$ |

TABLE 2

| A | $(R^1)_1$ | Position for substitution of $CH_2$—E | E | $(R^{12})_n$ |
|---|---|---|---|---|
| $CH_2CH_2NHCO_2C_2H_5$ | 2-Cl | 5 | $E_1$ | 3-$CH_3$ |
| $CH_2CH_2NHCO_2C_2H_5$ | 2-Cl | 4 | $E_2$ | 4-$CH_3$ |
| $CH_2CH_2NHCO_2C_2H_5$ | 2-Cl | 5 | $E_1$ | 5-$CH_3$ |
| $CH_2CH_2NHCO_2C_2H_5$ | 2-Cl | 4 | $E_1$ | 3,5-$CH_3$ |
| $CH_2CH_2NHCO_2C_2H_5$ | 2-Cl | 4 | $E_1$ | 4-Cl |
| $CH_2CH_2NHCO_2C_2H_5$ | 2-Cl | 5 | $E_2$ | 4-$CH_3$ |
| $CH_2CH_2NHCO_2C_2H_5$ | 2-Cl | 5 | $E_2$ | 4-Cl |
| $CH_2CH_2NHCO_2C_2H_5$ | 2-Cl | 5 | $E_1$ | 4-Cl |
| $CH_2CH_2NHCO_2C_2H_5$ | 2-Cl | 4 | $E_1$ | 4-Br |
| $CH_2CH_2NHCO_2C_2H_5$ | 2-Cl | 4 | $E_2$ | 4-Br |
| $CH_2CH_2NHCO_2C_2H_5$ | 2-Cl | 4 | $E_2$ | H |
| $CH_2CH_2NHCO_2C_2H_5$ | 2-Cl | 5 | $E_1$ | H |
| $CH_2CH_2NHCO_2C_2H_5$ | 2-Cl | 5 | $E_2$ | H |
| $CH_2CH_2NHCO_2C_2H_5$ | 2-Cl | 4 | $E_2$ | H |
| $CH_2CH_2NHCO_2C_2H_5$ | 2-Cl | 5 | $E_1$ | 3,5-$CH_3$ |
| $CH_2CH_2NHCO_2C_2H_5$ | 2-Cl | 4 | $E_1$ | 4-$CH_3$ |
| $CH_2CH_2NHCO_2C_2H_5$ | 2-Cl | 5 | $E_1$ | 4-$CH_3$ |
| $CH_2CH_2NHCO_2$-i-$C_3H_7$ | H | 4 | $E_1$ | H |
| $CH_2CH_2NHCO_2$-n-$C_3H_7$ | H | 4 | $E_1$ | H |
| $CH_2CH_2NHCO_2$-n-$C_4H_9$ | H | 3 | $E_1$ | H |

TABLE 2-continued

| A | $(R^1)_1$ | Position for substitution of $CH_2$—E | E | $(R^{12})_n$ |
|---|---|---|---|---|
| $CH_2CH_2NHCO_2CH_2CF_3$ | H | 4 | $E_1$ | H |
| $CH_2CH_2NHCO_2CH_2CH_2Cl$ | H | 4 | $E_1$ | H |

TABLE 3

| A | $(R^1)_1$ | Position for substitution of $CH_2$—E | E | $(R^{12})_n$ |
|---|---|---|---|---|
| $CH_2CH_2NHCO_2CH_2CH_2F$ | H | 4 | $E_1$ | H |
| $CH_2CH_2NHCO_2CH_2CH_2OCH_3$ | H | 4 | $E_1$ | H |
| $CH_2CH_2NHCO_2CH_2CH=CH_2$ | H | 4 | $E_1$ | H |
| $CH_2CH_2NHCO_2CH_2CCl=CH_2$ | H | 4 | $E_1$ | H |
| $CH_2CH_2NHCO_2CH_2C\equiv CH$ | H | 4 | $E_1$ | H |
| $CH_2CH_2NHCO_2CH_2C\equiv CCF_3$ | H | 4 | $E_1$ | H |
| $CH_2CH_2NHC(=O)SC_2H_5$ | H | 4 | $E_1$ | H |
| $CH_2CH_2CH_2NHCO_2C_2H_5$ | H | 3 | $E_1$ | H |
| $CH_2CH_2NHC(=S)OC_2H_5$ | H | 4 | $E_1$ | H |
| $CH_2CH_2NHCS_2C_2H_5$ | H | 4 | $E_1$ | H |
| $CH(CH_3)CH_2NHCO_2C_2H_5$ | H | 4 | $E_1$ | H |
| $CH_2CH(CH_3)NHCO_2C_2H_5$ | H | 4 | $E_1$ | H |
| $CH_2CH_2N(CH_3)CO_2C_2H_5$ | H | 4 | $E_1$ | H |
| $CH(CH_3)CH_2NHCO_2C_2H_5$ | H | 4 | $E_2$ | H |
| $CH_2CH_2NHC(=O)SC_2H_5$ | H | 4 | $E_2$ | H |
| $CH_2CH_2NHCO_2C_2H_5$ | 2-Br | 4 | $E_2$ | H |
| $CH_2CH_2NHCO_2CH_3$ | 2-Cl | 4 | $E_2$ | H |
| $CH_2CH_2NHCO_2CH_3$ | 2-Cl | 3 | $E_1$ | H |
| $CH_2CH_2NHCO_2CH_3$ | 2-Cl | 4 | $E_3$ | H |
| $CH_2CH_2NHCO_2CH_3$ | 2-Cl | 3 | $E_2$ | H |
| $CH_2CH_2NHCO_2CH_3$ | H | 4 | $E_1$ | 4-Cl |
| $CH_2CH_2NHCO_2CH_3$ | 2-Cl | 4 | $E_1$ | 4-Cl |

TABLE 4

| A | $(R^1)_1$ | Position for substitution of $CH_2$—E | E | $(R^{12})_n$ |
|---|---|---|---|---|
| $CH_2CH_2NHCO_2CH_3$ | H | 4 | $E_3$ | 3-Cl |
| $CH_2CH_2OC(=O)NHC_2H_5$ | H | 4 | $E_2$ | H |
| $CH_2CH_2OC(=O)NHC_2H_5$ | H | 4 | $E_3$ | H |
| $CH_2CH_2OC(=O)NHC_2H_5$ | H | 3 | $E_1$ | H |
| $CH_2CH_2OC(=O)NHC_2H_5$ | H | 4 | $E_1$ | 3-$CH_3$ |
| $CH_2CH_2OC(=O)NHC_2H_5$ | H | 4 | $E_1$ | 5-$CH_3$ |
| $CH_2CH_2OC(=O)NHC_2H_5$ | H | 4 | $E_1$ | 3,5-$CH_3$ |
| $CH_2CH_2OC(=O)NHC_2H_5$ | H | 4 | $E_1$ | H |
| $CH_2CH_2OC(=O)NHC_2H_5$ | H | 4 | $E_2$ | 4-Cl |
| $CH_2CH_2OC(=O)NHC_2H_5$ | H | 3 | $E_1$ | H |
| $CH_2CH_2OC(=O)NHC_2H_5$ | 2-Cl | 4 | $E_1$ | H |
| $CH_2CH_2OC(=O)NHC_2H_5$ | 2-$CH_3$ | 4 | $E_1$ | H |
| $CH_2CH_2OC(=O)N(CH_3)_2$ | H | 4 | $E_1$ | H |
| $CH_2CH_2OC(=O)NHCH_3$ | H | 4 | $E_1$ | H |
| $CH_2CH_2OC(=O)NH$-iso-$C_3H_7$ | H | 4 | $E_1$ | H |
| $CH_2CH_2OC(=O)NHCH_2CF_3$ | H | 4 | $E_1$ | H |
| $CH_2CH_2OC(=O)NHCH_2CH=CH_2$ | H | 4 | $E_1$ | H |
| $CH_2CH_2OC(=O)NHCH_2C\equiv CH$ | H | 4 | $E_1$ | H |
| $CH_2CH_2CH_2OC(=O)NHC_2H_5$ | H | 4 | $E_1$ | H |
| $CH_2CH_2SC(=O)NHC_2H_5$ | H | 4 | $E_1$ | H |
| $CH_2CH_2SC(=O)N(CH_3)_2$ | H | 4 | $E_1$ | H |
| $CH_2CH_2SC(=S)N(CH_3)_2$ | H | 4 | $E_1$ | H |

TABLE 5

| A | $(R^1)_1$ | Position for substitution of $CH_2$—E | E | $(R^{12})_n$ |
|---|---|---|---|---|
| $CH(CH_3)CH_2OC(=O)NHC_2H_5$ | H | 4 | $E_1$ | H |
| $CH_2CH(CH_3)OC(=O)NHC_2H_5$ | H | 4 | $E_1$ | H |
| $CH_2CH_2OC(=S)NHC_2H_5$ | H | 4 | $E_1$ | H |
| $CH_2CH_2CH_2OCH_2CH(CH_3)_2$ | H | 4 | $E_1$ | H |
| $CH_2CH_2CH_2OC_2H_5$ | H | 4 | $E_2$ | H |
| $CH_2CH_2CH_2OC_2H_5$ | H | 3 | $E_1$ | H |
| $CH_2CH_2CH_2O$-n-$C_3H_7$ | H | 4 | $E_1$ | H |
| $CH_2CH_2CH_2OCH_2CH=CH_2$ | H | 4 | $E_1$ | H |
| $CH_2CH_2CH_2OCH_2C(CH_3)=CH_2$ | H | 4 | $E_1$ | H |
| $CH_2CH_2CH_2OCH_2C\equiv CH$ | H | 4 | $E_1$ | H |
| $CH_2CH(CH_3)CH_2OCH_2CH(CH_3)_2$ | H | 4 | $E_1$ | H |
| $CH_2CH_2NHCO_2CH_3$ | 2-Cl | 4 | $E_3$ | 5-Cl |
| $CH_2CH_2NHCO_2C_2H_5$ | 2-Cl | 4 | $E_3$ | 5-Cl |
| $CH_2CH_2NHCO_2CH_3$ | H | 4 | $E_3$ | 5-Cl |
| $CH_2CH_2NHCO_2C_2H_5$ | H | 4 | $E_3$ | 5-Cl |
| $CH_2CH_2NHCO_2$-iso-$C_3H_7$ | H | 4 | $E_3$ | 5-Cl |
| $CH_2CH_2NHCO_2C_2H_5$ | H | 4 | $E_3$ | H |
| $CH_2CH_2NHCO_2CH_3$ | H | 4 | $E_3$ | H |
| $CH_2CH_2NHCO_2C_2H_5$ | 2-Cl | 4 | $E_3$ | H |
| $CH_2CH_2NHCO_2C_2H_5$ | 2-F | 4 | $E_3$ | H |
| $CH_2CH_2NHCO_2C_2H_5$ | 2,5-Cl | 4 | $E_3$ | H |
| $CH_2CH_2NHCO_2C_2H_5$ | 2-Cl | 5 | $E_3$ | H |

TABLE 6

| A | $(R^1)_1$ | Position for substitution of $CH_2$—E | E | $(R^{12})_n$ |
|---|---|---|---|---|
| $CH_2CH_2NHCO_2$-iso-$C_3H_7$ | 2-Cl | 4 | $E_3$ | H |
| $CH_2CH_2NHCO_2$-n-$C_3H_7$ | H | 4 | $E_3$ | H |
| $CH_2CH_2NHCO_2$-n-$C_4H_9$ | H | 4 | $E_3$ | H |
| $CH_2CH_2NHCO_2CH_2CF_3$ | H | 4 | $E_3$ | H |
| $CH_2CH_2NHCO_2CH_2CH_2Cl$ | H | 4 | $E_3$ | H |
| $CH_2CH_2NHCO_2CH_2CH_2F$ | H | 4 | $E_3$ | H |
| $CH_2CH_2NHCO_2CH_2CH_2OCH_3$ | H | 4 | $E_3$ | H |
| $CH_2CH_2NHCO_2C_2H_5$ | H | 4 | $E_3$ | 3-Cl |
| $CH_2CH_2NHCO_2CH_2CH=CH_2$ | H | 4 | $E_3$ | H |
| $CH_2CH_2NHCO_2CH_2CCl=CH_2$ | H | 4 | $E_3$ | H |
| $CH_2CH_2NHCO_2CH_2C\equiv CH$ | 2-Cl | 4 | $E_3$ | H |
| $CH_2CH_2NHCO_2CH_2C\equiv CCF_3$ | H | 4 | $E_3$ | H |
| $CH_2CH_2NHC(=O)SC_2H_5$ | H | 4 | $E_3$ | H |
| $CH_2CH_2NHC(=S)OC_2H_5$ | 2-Cl | 4 | $E_3$ | H |
| $CH_2CH_2NHCS_2C_2H_5$ | H | 4 | $E_3$ | H |
| $CH(CH_3)CH_2NHCO_2C_2H_5$ | H | 4 | $E_3$ | H |
| $CH_2CH(CH_3)NHCO_2C_2H_5$ | H | 4 | $E_3$ | H |
| $CH_2CH_2N(CH_3)CO_2C_2H_5$ | H | 4 | $E_3$ | H |
| $CH(CH_3)CH_2NHCO_2C_2H_5$ | H | 3 | $E_3$ | H |
| $CH_2CH_2NHCO(=O)SC_2H_5$ | H | 4 | $E_3$ | H |
| $CH_2CH_2NHCO_2$-iso-$C_3H_7$ | H | 4 | $E_3$ | H |
| $CH_2CH_2OC(=O)NHC_2H_5$ | H | 4 | $E_3$ | H |

TABLE 7

| A | $(R^1)_1$ | Position for substitution of $CH_2$—E | E | $(R^{12})_n$ |
|---|---|---|---|---|
| $CH_2CH_2NHCO_2C_2H_5$ | H | 4 | $E_3$ | 5-$CF_3$ |
| $CH_2CH_2NHCO_2C_2H_5$ | H | 4 | $E_3$ | 3-Cl, 5-$CF_3$ |
| $CH_2CH_2NHCO_2C_2H_5$ | H | 4 | $E_3$ | 3,5-$Cl_2$ |
| $CH_2CH_2NHCO_2C_2H_5$ | H | 4 | $E_3$ | 4-$CF_3$ |
| $CH_2CH_2NHCO_2C_2H_5$ | H | 4 | $E_3$ | 3-$CF_3$ |
| $CH_2CH_2OC(=O)NHC_2H_5$ | 2-Cl | 4 | $E_3$ | H |
| $CH_2CH_2NHCO_2C_2H_5$ | H | 4 | $E_3$ | 3-$CF_3$, 5-Cl |
| $CH_2CH_2NHCO_2C_2H_5$ | 2-Cl | 4 | $E_3$ | 5-$CF_3$ |
| $CH_2CH_2NHCO_2C_2H_5$ | 2-Cl | 4 | $E_3$ | 3-Cl, 5-$CF_3$ |
| $CH_2CH_2NHCO_2$-iso-$C_3H_7$ | H | 4 | $E_3$ | 3-Cl |

TABLE 7-continued

| A | $(R^1)_1$ | Position for substitution of $CH_2$—E | E | $(R^{12})_n$ |
|---|---|---|---|---|
| $CH_2CH_2NHC(=O)$-c-$C_3H_5$ | H | 4 | $E_1$ | H |
| $CH_2CH_2NHC(=S)$-c-$C_3H_5$ | H | 4 | $E_1$ | H |
| $CH_2CH_2NHC(=O)$-c-$C_3H_5$ | 2-Cl | 4 | $E_1$ | H |
| $CH_2CH_2NHC(=O)$-c-$C_3H_5$ | 2-Cl | 4 | $E_2$ | H |
| $CH_2CH_2NHC(=O)$-c-$C_3H_5$ | 2-Br | 4 | $E_1$ | H |
| $CH_2CH_2NHC(=O)$-c-$C_3H_5$ | 2-F | 4 | $E_1$ | H |
| $CH(CH_3)CH_2NHC(=O)$-c-$C_3H_5$ | 2-Cl | 4 | $E_1$ | H |
| $CH_2CH(CH_3)NHC(=O)$-c-$C_3H_5$ | H | 4 | $E_2$ | H |
| $CH_2CH_2OC(=O)$-c-$C_3H_5$ | H | 4 | $E_1$ | H |
| $CH_2CH_2OC(=O)$-c-$C_3H_5$ | 2-Cl | 4 | $E_1$ | H |

(wherein c-$C_3H_5$ represents cyclopropyl.)

TABLE 8

| A | $(R^1)_1$ | Position for substitution of $CH_2$—E | E | $(R^{12})_n$ |
|---|---|---|---|---|
| $CH_2CH_2CH_2$Pyra | H | 4 | $E_1$ | H |
| $CH_2CH_2CH_2$Pyra | H | 4 | $E_1$ | 4-Cl |
| $CH_2CH_2CH_2$Pyra | H | 4 | $E_2$ | H |
| $CH_2CH_2CH_2$Pyra | H | 3 | $E_1$ | H |
| $CH_2CH_2CH_2$Pyra | H | 4 | $E_3$ | H |
| $CH_2CH_2CH_2$Pyra | 2-Cl | 4 | $E_1$ | H |
| $CH_2CH_2CH_2$Pyra | 2-Cl | 4 | $E_1$ | 4-Cl |
| $CH_2CH_2CH_2$Pyra | 2-Cl | 3 | $E_1$ | H |
| $CH_2CH_2CH_2$Pyra | 2-Cl | 4 | $E_2$ | H |
| $CH_2CH_2CH_2$Pyra | 2-Cl | 4 | $E_3$ | H |
| $CH_2CH_2CH_2$Pyra | H | 4 | $E_3$ | 5-Cl |
| $CH_2CH_2CH_2$Pyra | H | 4 | $E_3$ | 3-$CF_3$, 5-Cl |
| $CH_2CH_2CH_2$Pyra | H | 4 | $E_3$ | 5-$CF_3$ |
| $CH_2CH_2CH_2$Pyra | 2-F | 4 | $E_1$ | H |
| $CH_2CH_2CH_2$Pyra | H | 4 | $E_3$ | 5-Cl |

(wherein Pyra represents pyrazol-1-yl.)

TABLE 9

| A | $(R^1)_1$ | Position for substitution of $CH_2$-E | E | $(R^{12})_n$ |
|---|---|---|---|---|
| $CH_2CH_2CH_2$Tr | H | 4 | $E_1$ | H |
| $CH_2CH_2CH_2$Tr | H | 4 | $E_1$ | 4-Cl |
| $CH_2CH_2CH_2$Tr | H | 4 | $E_2$ | H |
| $CH_2CH_2CH_2$Tr | H | 3 | $E_1$ | H |
| $CH_2CH_2CH_2$Tr | H | 4 | $E_3$ | H |
| $CH_2CH_2CH_2$Tr | 2-Cl | 4 | $E_1$ | H |
| $CH_2CH_2CH_2$Tr | 2-Cl | 4 | $E_1$ | 4-Cl |
| $CH_2CH_2CH_2$Tr | 2-Cl | 3 | $E_1$ | H |
| $CH_2CH_2CH_2$Tr | 2-Cl | 4 | $E_2$ | H |
| $CH_2CH_2CH_2$Tr | 2-Cl | 4 | $E_3$ | 5-Cl |
| $CH_2CH_2CH_2$Tr | H | 4 | $E_3$ | 5-Cl |

(wherein Tr represents 2H-1,2,3-triazol-2-yl.)

TABLE 10

| A | $(R^1)_1$ | Position for substitution of $CH_2$-E | E | $(R^{12})_n$ |
|---|---|---|---|---|
|  | H | 4 | $E_1$ | H |

TABLE 10-continued
| A | (R¹)₁ | Position for substitution of CH₂-E | E | (R¹²)ₙ |
|---|---|---|---|---|
| 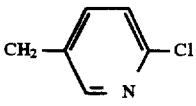 | H | 4 | $E_1$ | H |
| 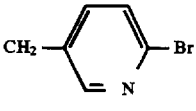 | H | 4 | $E_1$ | H |
| 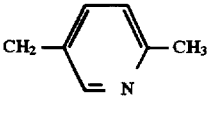 | H | 4 | $E_1$ | H |
| 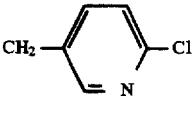 | 2-Cl | 4 | $E_1$ | H |
| 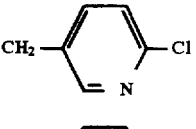 | 2-Cl | 4 | $E_2$ | H |
| 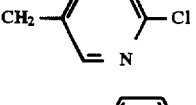 | H | 4 | $E_1$ | 4-Cl |
| 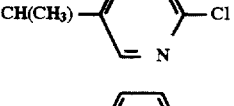 | H | 4 | $E_1$ | H |
| 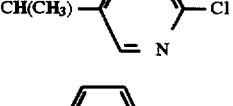 | 2-Cl | 4 | $E_1$ | H |
| 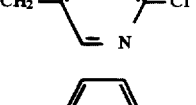 | H | 4 | $E_3$ | 5-Cl |
| 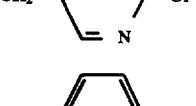 | 2-F | 4 | $E_1$ | H |
| 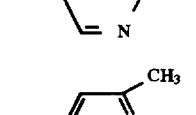 | 2-Cl | 5 | $E_1$ | H |
| 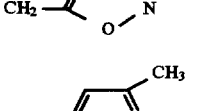 | H | 4 | $E_1$ | H |
| 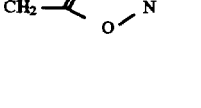 | 2-Cl | 4 | $E_1$ | H |
TABLE 10-continued
| A | (R¹)₁ | Position for substitution of CH₂-E | E | (R¹²)ₙ |
|---|---|---|---|---|
| 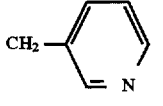 | H | 4 | $E_3$ | H |
| 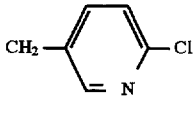 | H | 4 | $E_3$ | 3-Cl |
| 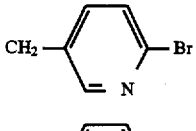 | H | 4 | $E_3$ | H |
| 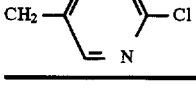 | 2-Cl | 4 | $E_3$ | H |
TABLE 11
| A | (R¹)₁ | Position for substitution of CH₂-E | E | (R¹²)ₙ |
|---|---|---|---|---|
| 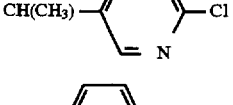 | H | 4 | $E_3$ | H |
| 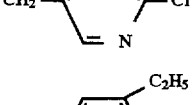 | H | 4 | $E_2$ | H |
| 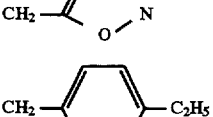 | H | 4 | $E_1$ | H |
| 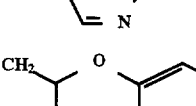 | H | 4 | $E_1$ | H |
| 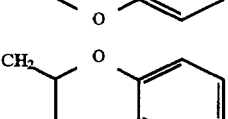 | H | 4 | $E_1$ | H |
| 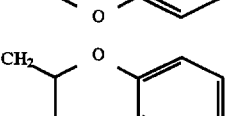 | 2-Cl | 4 | $E_1$ | H |
| 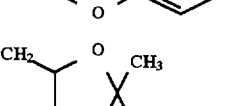 | H | 4 | $E_2$ | H |
| 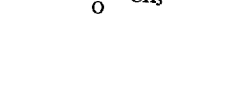 | H | 4 | $E_1$ | H |

TABLE 11-continued
| A | $(R^1)_1$ | Position for substitution of $CH_2$-E | E | $(R^{12})_n$ |
|---|---|---|---|---|
| 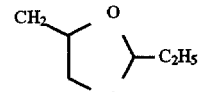 | 2-Cl | 4 | $E_1$ | H |
| 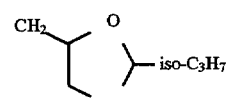 | 2-Br | 4 | $E_1$ | H |
| 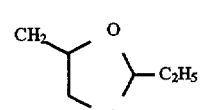 | 2-Cl | 5 | $E_2$ | H |
| 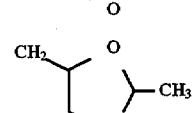 | H | 4 | $E_2$ | H |
| 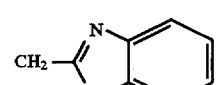 | H | 4 | $E_1$ | H |
| 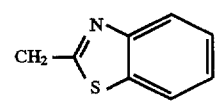 | 2-Cl | 4 | $E_1$ | H |
| 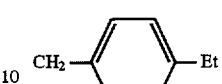 | 2-Br | 4 | $E_2$ | H |
| 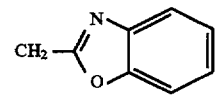 | 2-F | 4 | $E_1$ | H |
| 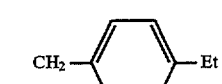 | H | 4 | $E_1$ | H |
| 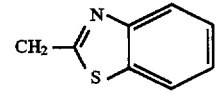 | H | 4 | $E_2$ | H |
(wherein Et represents ethyl.)
TABLE 12
| A | $(R^1)_1$ | Position for substitution of $CH_2$-E | E | $(R^{12})_n$ |
|---|---|---|---|---|
| 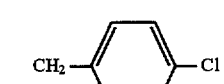 | H | 4 | $E_3$ | H |
| 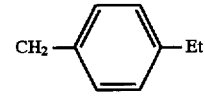 | 2-Cl | 4 | $E_1$ | H |
| 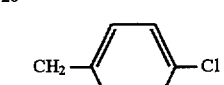 | 2-Cl | 4 | $E_2$ | H |
| 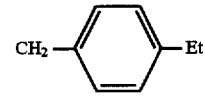 | 2-Cl | 4 | $E_3$ | H |
|  | 2-Cl | 4 | $E_1$ | H |
| 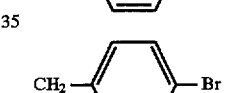 | 2-Cl | 4 | $E_2$ | H |
| 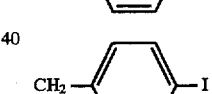 | 2-Cl | 4 | $E_3$ | H |
| 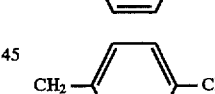 | 2-Cl | 4 | $E_1$ | H |
| 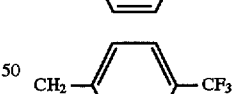 | 2-Cl | 4 | $E_1$ | H |
| 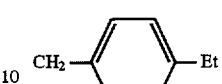 | 2-Cl | 4 | $E_1$ | H |
| 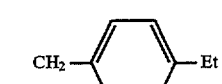 | 2-Cl | 4 | $E_1$ | H |
| 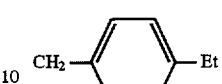 | 2-Cl | 4 | $E_1$ | H |
| 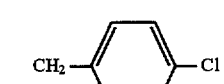 | 2-Cl | 4 | $E_1$ | H |
| 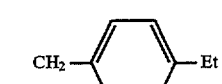 | 2-Cl | 4 | $E_1$ | H |
| 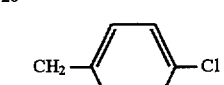 | 2-Cl | 4 | $E_2$ | H |

TABLE 12-continued

| A | $(R^1)_l$ | Position for substitution of $CH_2$-E | E | $(R^{12})_n$ |
|---|---|---|---|---|
| $CH_2$—〈phenyl〉 | 2-Cl | 4 | $E_1$ | H |
| $CH_2$—〈benzothiazole〉 | H | 4 | $E_3$ | H |
| $CH_2$—〈phenyl〉—Et | H | 4 | $E_3$ | 3-Cl |

(wherein Et represents ethyl.)

TABLE 13

| A | $(R^1)_l$ | Position for substitution of $CH_2$-E | E | $(R^{12})_n$ |
|---|---|---|---|---|
| $CH_2$—〈phenyl〉—Cl | H | 4 | $E_3$ | 3-Cl |
| $CH_2$—〈phenyl〉—Et | H | 4 | $E_3$ | 5-Cl |
| $CH_2$—〈phenyl〉—Cl | H | 4 | $E_3$ | 5-Cl |
| $CH_2$—〈pyridyl〉—Cl | H | 4 | $E_3$ | H |
| $CH_2CH_2CH_2$—〈phenyl〉 | H | 4 | $E_1$ | H |
| $CH_2CH_2CH_2$—〈pyridyl〉 | H | 4 | $E_1$ | H |
| $CH_2CH_2CH_2$—〈pyrimidinyl〉 | H | 4 | $E_1$ | H |
| $CH_2CH_2CH_2$—〈thiazolyl〉 | H | 4 | $E_1$ | H |
| $CH_2CH_2CH_2$—〈thiazolyl〉 | H | 4 | $E_1$ | H |

TABLE 13-continued

| A | $(R^1)_l$ | Position for substitution of $CH_2$-E | E | $(R^{12})_n$ |
|---|---|---|---|---|
| $CH_2CH_2CH_2$—〈phenyl〉 | H | 4 | $E_1$ | 4-Cl |
| $CH_2CH_2CH_2$—〈pyridyl〉 | H | 4 | $E_1$ | 4-Cl |
| $CH_2CH_2CH_2$—〈pyrimidinyl〉 | H | 4 | $E_1$ | 4-Cl |
| $CH_2CH_2CH_2$—〈thiazolyl〉 | H | 4 | $E_1$ | 4-Cl |
| $CH_2CH_2CH_2$—〈thiazolyl〉 | H | 4 | $E_1$ | 4-Cl |

The phenol derivatives of the general formula P-4 (including the phenol compounds of the general formula P-3) can be produced, for example, by hydrolyzing a phenol ester derivative of the general formula:

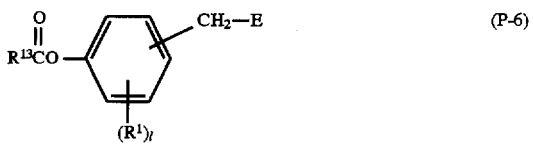

(P-6)

wherein $R^l$, E and l are as defined above and $R^{13}$ is $C_1$–$C_4$ alkyl (e.g., methyl, ethyl) or phenyl, in the presence of a base.

As the base which can be used, there can be mentioned, for example, alkali metal hydroxides such as sodium hydroxide and potassium hydroxide; alkaline earth metal hydroxides such as barium hydroxide; and alkali metal carbonates such as potassium carbonate and sodium carbonate.

This reaction is usually effected in a solvent. As the solvent which can be used, there can be mentioned, for example, alcohols such as methanol, ethanol, n-propyl alcohol, ethylene glycol and diethylene glycol; water; or mixtures thereof.

The reaction is usually effected in the range of 0° C. to 200° C. or the boiling point of the solvent used, preferably in the range of 20° C. to 120° C. The reaction time is usually 1 to 50 hours.

The amounts of the reagents to be used in the reaction, although the base can be used in any mole number, are preferably in the ratio of from 1 to 2 moles for the base, to 1 mole of the phenol ester derivative of the general formula P-6.

The phenol ester derivative of the general formula P-6 can be produced, for example, by reacting a phenol ester compound of the general formula:

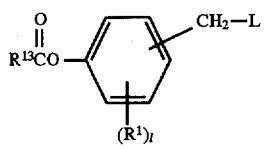 (P-7)

wherein $R^1$, $R^{13}$, l and L are as defined above, with a compound of the general formula:

E-H (P-8)

wherein E is as defined above, in the presence of a base.

This reaction is usually effected in an inert organic solvent. As the solvent which can be used, there can be mentioned, for example, aromatic hydrocarbons such as benzene, toluene, xylene and chlorobenzene; nitriles such as acetonitrile, propionitrile and isobutyronitrile; ketones such as acetone, methyl isobutyl ketone and methyl ethyl ketone; alcohols such as methanol, ethanol and n-propyl alcohol; ethers such as diethyl ether, diisopropyl ether, 1,2-diethoxyethane, tetrahydrofuran and dioxane; polar solvents such as N,N-dimethylformamide, N,N-dimethylacetamide, dimethylsulfoxide, sulforane and hexamethylphosphoric triamide; or mixtures thereof.

As the base which can be used, there can be mentioned, for example, alkali metals such as sodium and potassium; alkali metal hydroxides such as sodium hydroxide and potassium hydroxide; alkali metal carbonates such as sodium carbonate and potassium carbonate; alkali metal hydrides such as sodium hydride; alkali metal alkoxides (e.g., $C_1$–$C_4$ alkoxides such as methoxides and ethoxides) such as sodium ethoxide and sodium methoxide; and organic bases such as pyridine, triethylamine, N,N-dimethyl-aniline and 4-N,N-dimethylaminopyridine.

The reaction is usually effected in the range of 0° C. to 200° C. or the boiling point of the solvent used, preferably in the range of 20° C. to 120° C. The reaction time is usually 1 to 50 hours.

The amounts of reagents to be used in the reaction are usually in the ratio of from 1 to 10 moles, preferably from 1 to 2 moles, for each of the compound of the general formula P-8 and the base, to 1 mole of the phenol ester derivative of the general formula P-7.

Table 14 below show some typical examples of the phenol compound of the general formula P-3 [wherein $E_1$, $E_2$ and $E_3$ are as defined in Table 1 and the numbering of the position for substitution of $(R^{12})_n$ is as shown in Table 1].

TABLE 14

| E | $(R^{12})_n$ | E | $(R^{12})_n$ |
|---|---|---|---|
| $E_1$ | H | $E_1$ | 3-$CF_3$, 4-F |
| $E_1$ | 4-Cl | $E_1$ | 3-$CF_3$, 4-Cl |
| $E_1$ | 4-Br | $E_1$ | 3-$CF_3$, 4-Br |
| $E_1$ | 4-I | $E_1$ | 5-$CF_3$, 4-F |
| $E_1$ | 3-$CH_3$ | $E_1$ | 5-$CF_3$, 4-Cl |
| $E_1$ | 5-$CH_3$ | $E_1$ | 5-$CF_3$, 4-Br |
| $E_1$ | 3,5-$(CH_3)_2$ | $E_1$ | 3-$CF_3$, 5-$CH_3$ |
| $E_1$ | 4-$CH_3$ | $E_1$ | 3-$CH_3$, 5-$CF_3$ |
| $E_1$ | 4-Br, 3-$CH_3$ | $E_3$ | H |
| $E_1$ | 4-Br, 5-$CH_3$ | $E_2$ | 4-$CF_3$ |
| $E_1$ | 4-Br, 3,5-$(CH_3)_2$ | $E_2$ | 4-$CH_3$ |
| $E_1$ | 3-$CF_3$ | | |
| $E_1$ | 5-$CF_3$ | | |
| $E_1$ | 4-$CF_3$ | | |
| $E_2$ | H | | |

The present compounds exhibit excellent controlling effects against harmful organisms, for example, noxious insects and noxious ticks and mites, such as described below:

Noxious insects of Hemiptera planthoppers (Delphacidae) such as brown rice planthopper (*Nilaparvata lugens*), white-backed rice planthopper (*Sogatella furcifera*) and small brown planthopper (*Laodelphax striatellus*); leafhoppers (Deltocephalidae) such as green rice leafhopper (*Nephotettix cincticeps*), green rice leafhopper (*Nephotettix virescens*), green rice leafhopper (*Nephotettix nigropictus*), zig-zag rice leafhopper (*Recilia dorsalis*), tea green leafhopper (*Empoasca onukii*) and grape leafhopper (*Arboridia apicalis*); aphids (Aphididae) such as cotton aphid (*Aphis gossypii*) and green peach aphid (*Myzus persicae*); stink bugs (Pentatomidae); whiteflies (Aleyrodidae) such as sweetpotato whitefly (*Bemisia tabaci*) and greenhouse whitefly (*Trialeurodes vaporariorum*); scale insects (Coccidae); lace bugs (Tingidae); psyllids (Psyllidae), etc.

Noxious insects of Lepidoptera pyralid moths (Pyralidae) such as rice stem borer (*Chilo suppressalis*), rice leafroller (*Cnaphalocrocis medinalis*) and Indian meal moth (*Plodia interpunctella*); owlet moths (Noctuidae) such as common cutworm (*Spodoptera litura*), rice armyworm (*Spodoptera exigua*) and cabbage armyworm (*Mamestra brassicae*); white and sulfer butterflies (Pieridae) such as common cabbageworm (*Pieris rapae crucivora*); tortricid moths (Tortricidae) such as Adoxophyes spp.; Carposinidae; lionetiid moths (Lyonetidae); leaf-blotch miners (Gracillariidae); gelechiid moths (Gelechiidae); tussock moths (Lymantriidae); Plusiae; Agrotis spp. such as cutworm (*Agrotis segetum*) and black cutworm (*Agrotis ipsilon*); Heliothis spp.; diamondback moth or cabbage moth (*Plutella xylostella*); casemaking clothes moth or case-bearing clothes moth (*Tinea pellionella*); webbing clothes moth or common clothes moth (*Tineola bisselliella*), etc.

Noxious insects of Diptera mosquitos (Calicidae) such as common mosquito (*Culex pipiens pallens*) and *Gules tritaeniorhynchus*; Aedes spp. such as *Aedes aegypti* and *Aedes albopictus*; Anopheles spp. such as *Anophelinae sinensis*; midges (Chironomidae); house flies (Muscidae) such as house fly (*Musca domestica*) and false stablefly (*Muscina stabulans*); Calliphoridae; Sarcophagidae; anthomyild flies (Anthomyiidae) such as lesser housefly (*Fannia canicularis*), seedcorn maggot (*Hylemya platura*) and onion maggot (*Hylemya antique*); gall midges (Cecidornyiidae); fruit flies (Tephritidae); shore flies (Ephydridae); small fruit flies (Drosophilidae); moth flies (Psychodidae); black flies (Sirnuliidae); Tabanidae; stable flies (Stomoxyidae), etc.

Noxious insects of Coleoptera corn rootworms such as western corn rootworm (*Diabrotica virgifera*) and southern corn rootworm (*Diabrotica undecimpunctata*); scarabs (Scarabaeidae) such as cupreous chafer (*Anomala cuprea*) and soybean beetle (*Anomala rufocuprea*); weevils (Curculionidae) such as maize weevil (*Sitophilus zeamais*), rice water weevil (*Lissorphoptrus oryzophilus*) and azuki bean weevil (*Calosobruchys chincrisis*); darkling beeries (Tenebrionidae) such as yellow mealworm (*Tenebrio molitor*) and red flour beetle (*Tribolium castaneum*); lef beetles (Chrysomelidae) such as striped flea beetle (*Phyllotreta striolata*) and cucurbit leaf beetle (*Aulacophora femoralis*); drugstore beetles (Anobiidae); Epilachna spp. such as twenty-eight-spotted ladybird (*Epilachna vigintiocto-punctata*); powder post beetles (Lyctidae); false powderpost beetles (Bostrychidae); longhorn beetles (Cerambycidae), etc.

Noxious insects of Dictyoptera

German cockroach (*Blattella germanica*), smokybrown cockroach (*Periplaneta fuliginosa*), American cockroach (*Periplaneta americana*), brown cockroach (*Periplaneta brunnea*), oriental cockroach (*Blatta orientalis*), etc.

Noxius insects of Thysanoptera

*Thrips palmi*, yellow tea thrips (*Scirtothrips dorsalis*), flower thrips (*Thrips hawaiiensis*), etc.

Noxious insects of Hymenoptera ants (Formicidae); sawflies (Tenthredinidae) such as cabbage sawfly (*Athalia rosae japonensis*), etc.

Noxious insects of Orthoptera mole crickets (Gryllotalpidae), grasshoppers (Acrididac), etc.

Noxious insects of Aphaniptera

*Purex irritans* etc.

Noxious insects of Anoplura

*Pediculus humanus capitis, Phthirus pubis*, etc.

Noxious insects of Isoptera

*Reticulitermes speratus*, Formosan subterranean termite (*Coptotermes formosanus*), etc.

Spider mites (Tetranychidae)

carmine spider mite (*Tetranychus cinnabarinus*), two-spotted spider mite (*Tetranychus urticae*), Kanzawa spider mite (*Tetranychus kazawai*), citrus red mite (*Panonychus citri*), fruit tree red spider mite (*Panonychus ulmi*), etc.

Ticks (Ixodidae)

*Boophilus microphus* etc.

House dust mites

Grain mites, Dermatophagoides, Cheyletid mites, Ornithonyssus, etc.

If the present compounds are used in combination with other insecticides and/or acaricides, the controlling effects achieved by the present compounds can find practical applications to more various places for use against a wider variety of noxious insects.

As the insecticide and/or acaricide, which are suitable for combined use, there can be mentioned, for example, organophosphorus compounds such as Fenitrothion [O,O-dimethyl O-(3-methyl-4-nitrophenyl)phosphorothioate], Fenthion [O,O-dimethyl O-(3-methyl-4-(methylthio)phenyl]phophorothioate], Diazinon [O,O-diethyl-O-2-isopropyl-6-methylpyrimidin-4-ylphosphorothioate], Chlorpyriphos [O,O-diethyl-O-3,5,6-tri-chloro2-pyridylphosphorothioate], Acephate [O,S-dimethylacetylphosphoramidothioate], Methidathion [S-2,3-dihydro-5-methoxy-2-oxo-1,3,4-thiadiazol-3-ylmethyl O,O-dimethylphosphorodithioate], Ethylthiometon [O,O-diethyl S-2-ethylthioethylphosphorodithioate], DDVP [2,2-dichlorovinyldimethylphosphate], Sulprofos [O-ethyl O-4-(methyl-thio)phenyl S-propylphosphorodithioate], Cyanophos [O-4-cyanophenyl O,O-dimethylphosphorothioate], Salithion [2-methoxy-4H-1,3,2-benzodioxaphosphinine-2-sulfide], Dimethoate [O,O-dimethyl-S-(N-methylcarbamoylmethyl)dithiophosphate], Phenthoate [ethyl 2-dimethoxyphosphinothioylthio(phenyl) acetate], Malathion [diethyl(dimethoxyphosphinothioylthio) succinate], Trichlorfon [dimethyl 2,2,2-trichloro-1-hydroxyethylphosphonate], Azinphos-methyl [S-3,4-dihydro-4-oxy-1,2,3-benzotriazin-3-ylmethyl O,O-dimethylphosphorodithioate]and Monocrotophos [dimethyl (E)-1-methyl-2-(methylcarbamoyl)vinylphosphate]; carbamate compounds such as BPMC [2-sec-butylphenylmethylcarbamate], Benfuracarb [ethyl N-[2,3-dihydro-2,2-dimethylbenzofuran-7-yloxy-carbonyl(methyl) aminothio]-N-isopropyl-β-alaninate], Propoxur [2-isopropoxyphenyl N-methylcarbamate], Carbosulfan [2,3-dihydro-2,2-dimethyl-7-benzo[b]furanyl N-dibutyl-aminothio-N-methylcarbamate], Carbaril [1-naphthyl-N-methylcarbamate], Methomyl [S-methyl-N-[(methylcarbamoyl)oxy]thioacetimidate], Ethiofencarb [2-(ethylthiomethyl)-phenylmethylcarbamate], Aldicarb [2-methyl-2-(methylthio)propanaldehyde O-methylcarbamoyloxime]and Oxamyl [N,N-dimethyl-2-methylcarbamoyloxyimino-2-(methylthio)acetamide]; pyrethroid compounds such as Etofenprox [2-(4-ethoxyphenyl)-2-methylpropyl-3-phenoxybenzylether], Fenvalerate [(RS)-α-cyano-3-phenoxybenzyl (RS)-2-(4-chlorophenyl)-3-methylbutyrate], Esfenvalerate [(S)-α-cyano-3-phenoxybenzyl (S)-2-(4-chlorophenyl)-3-methylbutyrate], Fenpropathrin [(RS)-α-cyano-3-phenoxybenzyl 2,2,3,3-tetramethylcyclopmpanecarboxylate], Cypermethrin [(RS)-α-cyano-3-phenoxybenzyl(1RS,3RS)-3-(2,2-dichlorovinyl)-2,2-dimethylcyclopropanecarboxylate], Permethrin [3-phenoxybenzyl (1RS,3RS)-(1RS,3RS)-3-(2,2-dichlorovinyl)-2,2-methylcyclo-propanecarboxylate], Cyhalothrin [(RS)-α-cyano-3-phenoxybenzyl (Z)-(1RS)-3-(2-chloro-3,3,3-trifluoropropenyl)-2,2-dimethylcyclopropanecarboxylate], Deltamethrin [(S)-α-cyano-m-phenoxybenzyl (1R,3R)-3-(2,2-dibromovinyl)-2,2-dimethylcyclopropanecarboxylate]and Cycloprothrin [(RS)-α-cyano-3-phenoxybenzyl (RS)-2,2-dichloro-1-(4-ethoxyphenyl)cyclopropanecarboxylate]; thiadiazine derivatives such as Buprofezin [2-tert-butylimino-3-isopropyl-5-phenyl-1,3,5-thiadiazin-4-one]; nitroimidazolidine derivatives such as Imidacloprid [1-(6-chloro-3-pyridylmethyl)-N-nitroimidazolidin-2-ylidenamine]; Nereistoxin derivatives such as Cartap [S,S'-(2-dimethylaminotrimethylene)-bis(thiocarbamate)], Thiocyclam [N,N-dimethyl-1,2,3-trithian-5-ylamine] and Bensultap [S,S'-2-dimethylaminotrimethylene di(benzenethiosulfonate)]; chlorinated hydrocarbon compounds such as Endosulfan [6,7,8,9,10,10-hexachloro-1,5,5a,6,9,9a-hexahydro-6,9-methano-2,4,3-benzodioxathiepinoxide] and γ-BHC [1,2,3,4,5,6-hexachlorocyclohexane]; benzoylphenylurea compounds such as Chlorfluazuron [1-(3,5-dichloro-4-(3-chloro-5-trifluoromethylpyridin-2-yloxy)phenyl)-3-(2,6-difluorobenzoyl)urea], Teflubenzuron [1 -(3,5-dichloro-2,4-difluorophenyl)-3-(2,6-difluorobenzoyl)urea]and Fulphenoxron [1-(4-(2-chloro-4-trifluoromethylphenoxy)-2-fluorophenyl)-3-(2,6-difluorobenzoyl)urea]; formamidine derivatives such as Amitraz [N,N'[(methylimino) dimethylidine]-di-2,4-xylidine] and Chlordimeform [N'-(4-chloro-2-methylphenyl)-N,N-dimethylmethanimidamide].

When used as the active ingredients of harmful-organism controlling agents, the present compounds, although they may be used as such without any addition of other ingredients, are usually used as formulations such as oil sprays, emulsifiable concentrates, wettable powders, flowable concentrates for water-based suspensions or water-based emulsions; granules, dusts, aerosols, heating fumigants, e.g., fumigants of the self-combustion type, chemical reaction type or porous ceramic plate type; ULV agents or poison baits, by mixing them with solid carders, liquid carders, gaseous carriers or baits, and, if necessary, adding surfactants and other adjuvants for use in formulation.

These formulations contain the present compounds as the active ingredients usually in a proportion of from 0.001% to 95% by weight.

As the solid carrier to be used for formulation, there can be mentioned, for example, fine powder or granules of clay materials (e.g., kaolin clay, diatomaceous earth, synthetic hydrated silicon oxide, bentonite, Fubasami clay, acid clay), various kinds of talc, ceramics and other inorganic minerals (e.g., sericite, quartz, sulfur, active carbon, calcium carbonate, hydrated silica) and chemical fertilizers (e.g., ammonium sulfate, ammonium phosphate, ammonium nitrate, urea, ammonium chloride). As the liquid carrier, there can be mentioned, for example, water, alcohols (e.g., methanol, ethanol), ketones (e.g., acetone, methyl ethyl ketone), aromatic hydrocarbons (e.g., benzene, toluene, xylene, ethylbenzene, methylnaphthalene), aliphatic hydrocarbons (e.g., hexane, cyclohexane, kerosine, gas oil), esters (e.g., ethyl acetate, butyl acetate), nitriles (e.g., acetonitrile, isobutyronitrile), ethers (e.g., diisopropyl ether, dioxane), acid amides (e.g., N,N-dimethylformamide, N,N-dimethylacetamide), halogenated hydrocarbons (e.g., dichloromethane, trichloroethane, carbon tetrachloride), dimethyl sulfoxide and vegetable oils (e.g., soybean oil, cottonseed oil). As the gaseous carrier or propellant, there can be mentioned, for example, flon gas, butane gas, LPG (liquefied petroleum gas), dimethyl ether and carbon dioxide.

As the surfactant, there can be mentioned, for example, alkyl sulfates, alkyl sulfonates, alkyl arylsulfonates, alkyl aryl ethers and their polyoxyethylene derivatives, polyethylene glycol ethers, polyhydric alcohol esters and sugar alcohol derivatives.

As the adjuvant for use in formulation, such as fixing agents or dispersing agents, there can be mentioned, for example, casein, gelatin, polysaccharides (e.g., starch powder, gum arabic, cellulose derivatives, alginic acid), lignin derivatives, bentonitc, sugars and synthetic water-soluble polymers (e.g., polyvinyl alcohol, polyvinyl pyrrolidone, polyacrylic acid). As the stabilizer, there can be mentioned, for example, PAP (isopropyl acid phosphate), BHT (2,6-di-tert-butyl-4-methylphenol), BHA (mixtures of 2-tert-butyl-4-methoxyphenol and 3-tert-butyl-4-methoxyphenol), vegetable oils, mineral oils, surfactants, fatty acids or their esters.

As the base material for fumigants of the self-combustion type, there can be mentioned, for example, combustion heat-generating agents such as nitrate salts, nitrite salts, guanidine salts, potassium chlorate, nitrocellulose, ethyl cellulose and wood powder; thermolysis stimulators such as alkali metal salts, alkaline earth metal salts, dicromates and cromates; oxygen suppliers such as potassium nitrate; combustion aids such as melamine and wheat starch; extending agents such as diatomaceous earth; and binders such as synthetic paste.

As the base material for fumigants of the chemical reaction type, there can be mentioned, for exmaple, exothermic agents such as sulfides, polysulfides, hydrosulfides and salt hydrates of alkali metals, and calcium oxide; catalytic agents such as carbonaceous materials, iron carbide and activated clay; organic foaming agents such as azodicarbonamide, benzenesulfonyl hydrazine, dinitropentamethylenetetramine, polystyrene and polyurethane; and fillers such as natural fiber chips and synthetic fiber chips.

As the base material for poison baits, there can be mentioned, for example, bait ingredients such as grain powder, vegetable oils, sugars and crystalline cellulose; antioxidants such as dibutylhydroxytoluene and nordihydroguaiaretic acid; preservatives such as dehydroacetic acid; feeding-error preventing agents such as red pepper powder; and attractant flavors such as cheese flavor and onion flavor.

The formulations such as flowable concentrates (for water-based suspensions or water-based emulsions) are usually obtained by suspending 1–75% compound in water containing 0.5–15% dispersing agents, 0.1–10% suspending agents (e.g., protective colloids or thixotropy-imparting compounds) and 0–1.0% appropriate adjuvants (e.g., defoaming agents, anti-corrosive agents, stabilizing agents, spreading agents, penetration aids, anti-freezing agents, anti-fungus agents, anti-smoking agents). Various oils in which the present compounds are substantially insoluble may be used instead of water to give oil-based suspensions. As the protective colloid, there can be mentioned, for example, gelatin, casein, various kinds of gum, cellulose ethers and polyvinyl alcohol. As the thixotropy-imparting compound, there can be mentioned, for example, bentonite, aluminum magnesium silicate, xanthane gum and polyacrylic acid.

The formulations thus obtained are used as such or after diluted with water or the like. They may be used, in admixture or without mixing, with other insecticides, nematocides, acaricides, fungicides, herbicides, plant growth regulators, synergists, fertilizers, soil conditioners, animal feed and the like.

When the present compounds are used as the harmful-organism controlling agents for agriculture, the application amount thereof is usually in the range of 0.001 to 500 g, preferably 0.1 g to 500 g, per 10 ares. Their formulations such as emulsifiable concentrates, wettable powders and flowable concentrates are usually used after diluted with water to an application concentration of 0.0001 to 1000 ppm. Their formulations such as granules and dusts are used as such without any dilution. When the present compounds are used as the harmful-organism controlling agents for epidemic prevention, their formulations such as emulsifiable concentrates, wettable powders and flowable concentrates are usually used after diluted with water to an application concentration of 0.0001 to 10000 ppm, and their formulations such as oil sprays, aerosols, fumigants, ULV agents and poison baits are used as such.

All of these application amounts and application concentrations may vary with the formulation type, application time, application place, application method, kind of harmful organisms such as noxious insects, noxious mites and ticks, degree of damage and other conditions, and they can be increased or decreased without limitation to the above range.

EXAMPLES

The present invention will be further illustrated by the following production examples, formulation examples and test examples; however, the present invention is not limited to these examples.

The following will describe production examples for the present compounds.

Production Example 1

4-(1-Pyrazolyl)methylphenol [this was obtained in the following manner: A mixture of pyrazole (351 mg), 4-acetoxybenzyl bromide (1 g), anhydrous potassium carbonate (1.30 g) and anhydrous N,N-dimethylformamide (30 ml) was heated at 100° C. under stirring for 3 hours. The reaction mixture was then poured into ice-cooled saturated aqueous ammonium chloride solution (200 ml), which was extracted twice with ethyl acetate (50 ml). The organic layers were combined, washed with saturated sodium chloride solution (50 ml), dried with anhydrous magnesium sulfate, and concentrated under reduced pressure. The residue was dissolved in ethanol (20 ml), to which 5N aqueous sodium hydroxide solution (1.03 ml) was added, and the mixture was stirred at room temperature overnight. Then, water (10 ml) was added to the reaction mixture, which was concentrated under reduced pressure to remove most of the ethanol. The residue was poured into an ice-cooled mixture of acetic acid (310 mg) and water (100 ml), which was extracted twice with ethyl acetate (50 ml). The organic layers were combined, washed with saturated sodium chloride solution, dried with anhydrous magnesium sulfate, and concentrated under reduced pressure.] was dissolved in anhydrous N,N-dimethylformamide (20 ml), to which 2-chloroethylcarbamic acid methyl ester (710 mg) and potassium carbonate (1.43 g) were added, and the mixture was heated at 60° C. under stirring for 6 hours. The reaction mixture was then poured into ice-cooled saturated aqueous ammonium chloride solution (100 ml), which was extracted twice with ethyl acetate (50 ml). The organic layers were combined, washed with saturated sodium chloride solution, dried with anhydrous magnesium sulfate, and concentrated under reduced pressure. The residue was subjected to silica gel chromatography, which afforded 128 mg of 2-[4-(1-pyrazolyl)methylphenoxy]ethylcarbamic acid methyl ester (compound 3). Yield, 10% (based upon 4-acetoxybenzyl bromide).

Production Example 2

To a mixture of potassium carbonate (435 mg), 2-chloro-4-(2-2H-1,2,3-tri-azolyl)methylphenol (300 mg) and anhydrous N,N-dimethylformamide (30 ml) was added dropwise an anhydrous N,N-dimethylformamide solution (2 ml) of 2-chloroethylcarbamic acid methyl ester (216 mg) at room temperature under stirring. This mixture was then heated at 60° C. under stirring for 6 hours, and poured into ice-cooled saturated aqueous ammonium chloride solution, which was extracted with ethyl acetate. The organic layer was washed with water and then saturated sodium chloride solution, dried with anhydrous magnesium sulfate, and concentrated under reduced pressure. The residue was subjected to silica gel chromatography, which afforded 329 mg of 2-[2-chloro-4-(1-pyrazolyl)methylphenoxy]ethylcarbamic acid methyl ester (compound 7). Yield, 74%.

Production Example 3

4-(1-Pyrazolyl)methylphenol [this was obtained by the method described in the square parentheses in Production Example 1 ] was dissolved in anhydrous N,N-dimethylformamide (20 ml), to which 2-chloroethylcarbamic acid ethyl ester (782 mg) and potassium carbonate (1.43 g) were added, and the mixture was heated at 60° C. under stirring for 6 hours. The reaction mixture was then poured into ice-cooled saturated aqueous ammonium chloride solution (100 ml), which was extracted twice with ethyl acetate (50 ml). The organic layers were combined, washed with saturated sodium chloride solution, dried with anhydrous magnesium sulfate, and concentrated under reduced pressure. The residue was subjected to silica gel chromatography, which afforded 149 mg of 2-[4-(1-pyrazolyl)methylphenoxy]ethylcarbamic acid ethyl ester (compound 1). Yield, 11% (based upon 4-acetoxybenzyl bromide).

Production Example 4

2-Chloro-4-(1-pyrazolyl)methylphenol [this was obtained in the following manner: A mixture of pyrazole (275 mg), 4-acetoxy-3-chlorobenzyl bromide (1 g), anhydrous potassium carbonate (1.11 g) and anhydrous N,N-dimethylformamide (30 ml) was heated at 100° C. under stirring for 3 hours. The reaction mixture was then poured into ice-cooled saturated aqueous ammonium chloride solution (200 ml), which was extracted twice with 50 ml of ethyl acetate. The organic layers were combined, washed with saturated sodium chloride solution (50 ml), dried with anhydrous magnesium sulfate, and concentrated under reduced pressure. The residue was dissolved in ethanol (20 ml), to which 5N aqueous sodium chloride solution (0.97 ml) was added, and the mixture was stirred at room temperature overnight. Then, water (10 ml) was added to the reaction mixture, which was concentrated under reduced pressure to remove most of the ethanol. The residue was poured into an ice-cooled mixture of acetic acid (291 mg) and water (100 ml), which was extracted twice with 50 ml of ethyl acetate. The organic layers were combined, washed with saturated sodium chloride solution, dried with anhydrous magnesium sulfate, and concentrated under reduced pressure.] was dissolved in anhydrous N,N-dimethylformamide (20 ml), to which 2-chloroethylcarbamic acid ethyl ester (613 mg) and potassium carbonate (1.23 g) were added, and the mixture was heated at 60° C. under stirring for 6 hours. The reaction mixture was then poured into ice-cooled saturated aqueous ammonium chloride solution (100 ml), which was extracted twice with ethyl acetate (50 ml). The organic layers were combined, washed with saturated sodium chloride solution, dried with anhydrous magnesium sulfate, and concentrated under reduced pressure. The residue was subjected to silica gel chromatography, which afforded 189 mg of 2-[2-chloro-4-(1-pyrazolyl)methylphenoxy]ethylcarbamic acid ethyl ester (compound 2). Yield, 14% (based upon 4-acetoxy-3-chlorobenzyl bromide).

Production Example 5

To a mixture of potassium carbonate (298 mg), 2-chloro-4-(1-pyrazolyl)methylphenol (300 mg) and anhydrous N,N-dimethylformamide (200 ml) was added dropwise an anhydrous N,N-dimethylformamide solution (2 ml) of 4-chlorobenzyl chloride (232 mg) at room temperature under stirring. This mixture was then stirred at the same temperature for 12 hours, and poured into ice-cooled saturated aqueous ammonium chloride solution, which was extracted with ethyl acetate. The organic layer was washed with water and then saturated sodium chloride solution, dried with anhydrous magnesium sulfate, and concentrated under reduced pressure. The residue was subjected to silica gel chromatography, which afforded 454 mg of 2-chloro-1-(4-chlorobenzyloxy)-4-(1-pyrazolyl)methylbenzene (compound 4). Yield, 95%.

Production Example 6

To a mixture of potassium carbonate (387 mg), 2-chloro-4-(2-pyridon-1-yl)-methylphenol (300 mg) and anhydrous N,N-dimethylformamide (200 ml) was added dropwise an anhydrous N,N-dimethylformamide solution (2 ml) of 2-chloroethylcarbamic acid ethyl ester (212 mg) at room temperature under stirring. This mixture was then stirred at 60° C. for 6 hours, and poured into ice-cooled saturated aqueous ammonium chloride solution, which was extracted with ethyl acetate. The organic layer was washed with water and then saturated sodium chloride solution, dried with anhydrous magnesium sulfate, and concentrated under reduced pressure. The residue was subjected to silica gel chromatography, which afforded 303 mg of 2-[2-chloro-4-(2-pyridon-1-yl)methylphenoxy]ethylcarbamic acid ethyl ester (compound 34). Yield, 68%.

Production Example 7

To a mixture of potassium carbonate (211 mg), 4-(5-chloro-2-pyridon-1-yl)-methylphenol (300 mg) and anhydrous N,N-dimethylformamide (20 ml) was added dropwise an anhydrous N,N-dimethylformamide solution (2 ml) of 2-chloro-5-(chloromethyl)pyridine (206 mg) at room temperature under stirring. This mixture was then stirred at the same temperature for 12 hours, and poured into ice-cooled saturated aqueous ammonium chloride solution, which was extracted with ethyl acetate. The organic layer was washed with water and then saturated sodium chloride solution, dried with anhydrous magnesium sulfate, and concentrated under reduced pressure. The residue was subjected to silica gel chromatography, which afforded 397 mg of 1-{(2-chloropyridin-5-yl)methyl-oxy}-4-{(5-chloro-2-pyridon-1-yl)methyl}benzene (compound 29). Yield, 87%.

Production Example 8

To a mixture of anhydrous N,N-dimethylformamide (5 ml) and sodium hydride (60% oil dispersion) (62 mg) was added pyrazole (100 mg), and the mixture was stirred for 30 minutes. An anhydrous N,N-dimethylformamide solution (5 ml) of 3-[4-(1-pyrazolyl)methylphenoxy]propylamide (produced in Reference Production Example 1 described below) (434 mg) was then added dropwise, and the mixture was stirred at room temperature for 5 hours. The reaction mixture was then diluted with ethyl acetate (50 ml), which was washed twice with saturated aqueous ammonium chloride solution, dried with anhydrous magnesium sulfate, and concentrated under reduced pressure. The resulting oil was subjected to silica gel column chromatography, which afforded 340 mg of 1-{3-[4-(1-pyrazolyl)methylphenoxy] propyl}pyrazole (compound 31) in colorless oil. Yield, 82%.

Production Example 9

To a mixture of 2-[4-(1-pyrazolyl)methylphenoxy] ethylamine (produced in Reference Production Example 2 described below) (300 mg), triethylamine (210 mg) and anhydrous toluene (20 ml) was added dropwise an anhydrous toluene solution (2 ml) of cyclopropanecarbonyl chloride (159 mg) while stirring under ice cooling. This mixture was then stirred at 0° to 10° C. for 1 hour, and poured into ice-cooled saturated aqueous ammonium chloride solution, which was extracted with ethyl acetate. The organic layer was washed with water and then saturated sodium chloride solution, dried with anhydrous magnesium sulfate, and concentrated under reduced pressure. The residue was subjected to silica gel chromatography, which afforded 100 mg of N-{2-[4-(1-pyrazolyl)-methylphenoxy] ethyl}cyclopropanecarboxamide (compound 14). Yield, 25%.

Production Example 10

To a mixture of 2-[4-(1-pyrazolyl)methylphenoxy]ethanol (produced in Reference Production Example 3 described below) (500 mg), triethylamine (255 mg) and dry toluene (20 ml) was added dropwise an anhydrous toluene solution (1 ml) of ethyl isocyanate (179 mg). This mixture was then stirred at room temperature overnight, and concentrated under reduced pressure. The residue was subjected to silica gel chromatography, which afforded 87 mg of ethylcarbamic acid 2-[4-(1-pyrazolyl)methylphenoxy]-ethyl ester (compound 37). Yield, 13%.

Production Example 11

A mixture of 4-(1-pyrazolyl)methylphenol [this was obtained by the same method as described in the square parentheses in Production Example 1] (2 g), glycidol (936 g), dry xylene (10 ml) and a catalytic amount of tetramethylammonium chloride was stirred at 60° C. for 6 hours. The reaction mixture was then subjected to silica gel chromatography, which afforded 941 mg of 2-hydroxy-3-[4-(1-pyrazolyl)methylphenoxy]-propanol.

A mixture of this 2-hydroxy-3-[4-(1-pyrazolyl) methylphenoxy]propanol (941 mg), propionaldehyde (308 mg), dry toluene (20 ml) and a catalytic amount of p-toluenesulfonic acid was heated at reflux under stirring for 4 hours. Then, the reaction mixture was poured into ice-cooled 5% aqueous sodium hydrogencarbonate (100 ml), followed by two extractions with ethyl acetate (50 ml). The organic layers were combined, washed with saturated sodium chloride solution, dried with anhydrous magnesium sulfate, and concentrated under reduced pressure. The residue was subjected to silica gel chromatography, which afforded 723 mg of 4-[4-(1-pyrazolyl)methylphenoxy]-methyl-2-ethyl-1,3-dioxolane (compound 38). Yield, 66% (based upon 2-hydroxy-3-[4-(1-pyrazolyl)methylphenoxy] propanol).

Some typical examples of the present compounds are shown together with their compound numbers and physical properties in Tables 15 to 18 (by the definition of each substituent in the compounds of the general formula P-1).

TABLE 15

| Compound No. | A | $(R^1)_l$ | Position for substitution of $CH_2-E$ | E | $(R^{12})_n$ | Physical properties |
|---|---|---|---|---|---|---|
| 1 | $CH_2CH_2NHCO_2Et$ | H | 4 | $E_1$ | H | m.p. 84.2' C. |
| 2 | $CH_2CH_2NHCO_2Et$ | 2-Cl | 4 | $E_1$ | H | $n_D^{24.0}$ 1.5379 |
| 3 | $CH_2CH_2NHCO_2Me$ | H | 4 | $E_1$ | H | m.p. 65.0° C. |
| 4 | 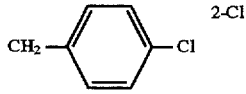 | 2-Cl | 4 | $E_1$ | H | m.p. 58.9° C. |
| 5 | 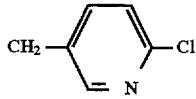 | 2-Cl | 4 | $E_1$ | H | m.p. 109.3° C. |
| 6 | $CH_2CH_2NHCO_2Me$ | 2-Cl | 4 | $E_1$ | H | m.p. 106.0° C. |

TABLE 15-continued

| Compound No. | A | $(R^1)_l$ | Position for substitution of $CH_2-E$ | E | $(R^{12})_n$ | Physical properties |
|---|---|---|---|---|---|---|
| 7 | $CH_2CH_2NHCO_2Me$ | 2-Cl | 4 | $E_2$ | H | m.p. 111–113° C. |
| 8 | $CH_2CH_2NHCO_2$-i-Pr | 2-Cl | 4 | $E_3$ | H | m.p. 84.2° C. |
| 9 | $CH_2$—(2-chloropyridin-4-yl) | 2-Cl | 4 | $E_3$ | H | m.p. 176.1° C. |
| 10 | $CH_2$—(4-chlorophenyl) | 2-Cl | 4 | $E_3$ | H | m.p. 143.0° C. |
| 11 | $CH_2$—(4-ethylphenyl) | 2-Cl | 4 | $E_3$ | H | m.p. 84.4° C. |
| 12 | $CH_2CH_2NHCO_2Et$ | H | 4 | $E_1$ | 4-Cl | m.p. 133.4° C. |

TABLE 16

| Compound No. | A | $(R^1)_l$ | Position for substitution of $CH_2-E$ | E | $(R^{12})_n$ | Physical properties |
|---|---|---|---|---|---|---|
| 13 | $CH_2$—(2-chloropyridin-4-yl) | H | 4 | $E_1$ | 4-Cl | m.p. 96.9° C. |
| 14 | $CH_2CH_2NHCO(=O)$-c-Pr | H | 4 | $E_1$ | H | m.p. 103.1° C. |
| 15 | $CH_2CH_2NHCO_2Et$ | H | 4 | $E_2$ | H | m.p. 85.2° C. |
| 16 | $CH_2$—(2-chloropyridin-4-yl) | H | 4 | $E_2$ | H | m.p. 117.2° C. |
| 17 | $CH_2$—(4-ethylphenyl) | H | 4 | $E_3$ | H | m.p. 85.5° C. |
| 18 | $CH_2CH_2NHCO_2$-i-Pr | H | 4 | $E_3$ | H | m.p. 86.8° C. |
| 19 | $CH_2$—(4-ethylphenyl) | H | 4 | $E_3$ | 3-Cl | m.p. 93.0° C. |
| 20 | $CH_2$—(4-chlorophenyl) | H | 4 | $E_3$ | 3-Cl | m.p. 82.7° C. |
| 21 | $CH_2CH_2NHCO_2Me$ | H | 4 | $E_3$ | 3-Cl | m.p. 109–110° C. |
| 22 | $CH_2CH_2NHCO_2Et$ | H | 4 | $E_3$ | 3-Cl | m.p. 127.3° C. |

(wherein the numbering of the positions for substitution of $(R^1)_l$, $CH_2-E$ and $(R^{12})_n$ in Tables 16 to 19 are the same as described in Table 1; $E_1$, $E_2$ and $E_3$ are as defined in Table 1; Et represents ethyl; Me, methyl; i-Pr, isopropyl; c-Pr, cyclopropyl; and Pyra, pyrazol-1-yl.)

TABLE 17

| Compound No. | A | $(R^1)_l$ | Position for substitution of $CH_2-E$ | E | $(R^{12})_n$ | Physical properties |
|---|---|---|---|---|---|---|
| 23 | $CH_2CH_2NHCO_2$-i-Pr | H | 4 | $E_3$ | 3-Cl | m.p. 114.8° C. |
| 24 | $CH_2$—⟨C$_6$H$_4$⟩—Et | H | 4 | $E_3$ | 5-Cl | m.p. 100.7° C. |
| 25 | $CH_2CH_2NHCO_2Me$ | H | 4 | $E_3$ | 5-Cl | m.p. 156.7° C. |
| 26 | $CH_2CH_2NHCO_2Et$ | H | 4 | $E_3$ | 5-Cl | m.p. 154.4° C. |
| 27 | $CH_2CH_2NHCO_2Et$ | H | 4 | $E_3$ | 5-Cl | m.p. 119~120° C. |
| 28 | $CH_2$—⟨C$_6$H$_4$⟩—Cl | H | 4 | $E_3$ | 5-Cl | m.p. 108.6° C. |
| 29 | $CH_2$—⟨pyridyl⟩—Cl | H | 4 | $E_3$ | 5-Cl | m.p. 171.6° C. |
| 30 | $CH_2$—⟨pyridyl⟩—Cl | H | 4 | $E_3$ | 3-Cl | m.p. 145~148° C. |
| 31 | $CH_2CH_2CH_2$Pyra | H | 4 | $E_1$ | H | m.p. 41.5~42.5° C. |
| 32 | $CH_2CH_2CH_2$Pyra | H | 4 | $E_1$ | 4-Cl | m.p. 66.6° C. |
| 33 | $CH_2CH_2CH_2$Pyra | 2-Cl | 4 | $E_1$ | H | m.p. 88.0° C. |
| 34 | $CH_2CH_2NHCO_2Et$ | 2-Cl | 4 | $E_3$ | H | m.p. 163.2° C. |

TABLE 18

| Compound No. | A | $(R^1)_l$ | Position for substitution of $CH_2-E$ | E | $(R^{12})_n$ | Physical properties |
|---|---|---|---|---|---|---|
| 35 | $CH_2CH_2NHC(=O)$-c-Pr | 2-Cl | 4 | $E_1$ | H | m.p. 131.1° C. |
| 36 | $CH_2CH_2OC(=O)NMe_2$ | H | 4 | $E_1$ | H | m.p. 99.8° C. |
| 37 | $CH_2CH_2OC(=O)NHEt$ | H | 4 | $E_1$ | H | m.p. 103.3° C. |
| 38 | $CH_2CH$—O—$CH$—Et (with $CH_2$—O bridge) | H | 4 | $E_1$ | H | m.p. 83.9° C. |
| 39 | $CH_2CH_2OC(=S)NHEt$ | H | 4 | $E_1$ | H | m.p. 105.9° C. |

The following will describe production examples for the intermediates of the general formula P-2.

Intermediate Production Example 1

Production of 2-chloro-4-(1-pyrazolyl)methylphenol (1) Production of 2-chloro-4-methylphenyl 2,2-dimethylpropanoate To a mixture of 2-chloro-4-methylphenol (100 g), triethylamine (92.3 g) and anhydrous tetrahydrofuran (1 liter) was added dropwise pivalic chloride (93.0 g) at 5° to 10° C. under stirring over 1 hour. Then, after stirring at the same temperature for 3 hours, the reaction mixture was poured into ice water, which was extracted with diethyl ether. The organic layer was washed with 3% aqueous hydrochloric acid solution and then water, dried with anhydrous magnesium sulfate, and concentrated under reduced pressure. The resulting oil was distilled under reduced pressure, which afforded 155.3 g of 2-chloro-4-methylphenyl 2,2-dimethylpropanoate as a colorless clear liquid. Yield, 97.7%. b.p., 113°–8° C./5 mmHg; $n_D^{21.8}$ 1.4949

(2) Production of 4-bromomethyl-2-chorophenyl 2,2-dimethylpropanoate

To a mixture of 2-chloro-4-methylphenyl 2,2-dimethylpropanoate (50.0 g), anhydrous sodium carbonate (23.8 g) and carbon tetrachloride (500 ml) was added a very small amount of benzoyl peroxide, and bromine (35.2 g) was added dropwise at 60° C. under stirring over 3 hours. While checking the progress of the reaction (the red color of bromine disappeared), a very small amount of benzoyl peroxide was added, if necessary, and stirring was continued until the reaction was thoroughly completed.

After completion of the reaction, the reaction mixture was cooled to 10° C., and undissolved matters were removed by filtration under suction, followed concentration under reduced pressure, which afforded 68.7 g of 4-bromomethyl 2-chlorophenyl 2,2-dimethylpropanoate as a pale yellow solid. Apparent yield, 101.7%. This solid was recrystallized from a mixed solvent of hexane and toluene to give white crystals.

m.p., 63.3° C.

(3) Production of 2-chloro-4-(1-pyrazolyl)methylphenyl 2,2-dimethylpropanoate

A mixture of pyrazole (15.3 g), sodium hydride (60%, 8.99 g) and anhydrous N,N-dimethylformamide (200 ml) was stirred at 60° to 70° C. under a nitrogen atmosphere for 2 hours. After the evolution of hydrogen gas ceased, the mixture was cooled to 10° C. To this mixture was added dropwise an anhydrous N,N-dimethylformamide (300 ml) solution of 4-bromomethyl-2-chlorophenyl 2,2-dimethylpropanoate (68 g) at room temperature under stirring over 1 hour, and the mixture was stirred at 80° C. for 1 hour. After cooling, the reaction mixture was poured into ice water, which was extracted with ethyl acetate. The organic layer was washed with saturated aqueous ammonium chloride solution and then saturated sodium chloride solution, dried with anhydrous magnesium sulfate, and concentrated under reduced pressure. The residue was subjected to silica gel column chromatography, which afforded 39.5 g of 2-chloro-4-(1-pyrazolyl)methylphenyl 2,2-dimethylpropanoate as a colorless oil. Yield, 60%.

$n_D^{21.8}$ 1.5461

(4) Production of 2-chloro-4-(1-pyrazolyl)methylphenol

A mixture of 2-chloro-4-(1-pyrazolyl)methylphenyl 2,2-dimethylpropanoate (20.0 g), 20% aqueous sodium hydroxide solution (50 ml) and ethanol (300 ml) was heated at reflux for 5 hours. The reaction mixture was then concentrated under reduced pressure, to which water was added, and the mixture was adjusted to pH 6.0 with concentrated hydrochloric acid. This mixture was extracted with ethyl acetate. The organic layer was washed with water, dried with anhydrous magnesium sulfate, and concentrated under reduced pressure. The residue was subjected to silica gel column chromatography, which afforded 11.5 g of 2-chloro-4-(1-pyrazolyl)methylphenyl as white crystals. Yield, 80.7%.

m.p., 152.9° C.

Intermediate Production Example 2

Production of 2-chloro-4-(2-2H-1,2,3-triazolyl) methylphenol (1) Production of 2-chloro-4-(2-2H-1,2,3-triazolyl) methylphenyl 2,2-dimethylpropanoate A mixture of 2H-1,2,3-triazole (2.26 g), sodium hydride (60%, 1.31 g) and anhydrous N,N-dimethylformamide (100 ml) was stirred at 60° to 70° C. under a nitrogen atmosphere for 2 hours. After the evolution of hydrogen gas ceased, the mixture was cooled to 10° C. To this mixture was added dropwise an anhydrous N,N-dimethylformamide (150 ml) solution of 4-bromomethyl-2-chlorophenyl 2,2-dimethylpropanoate (10 g) at room temperature under stirring over 1 hour, and the mixture was stirred at 80° C. for 1 hour. After cooling, the reaction mixture was poured into ice water, which was extracted with ethyl acetate. The organic layer was washed with saturated aqueous ammonium chloride solution and then saturated sodium chloride solution, dried with anhydrous magnesium sulfate, and concentrated under reduced pressure. The residue was subjected to silica gel column chromatography, which afforded 2-chloro-4-(2-2H-1,2,3-triazolyl)-methylphenyl 2,2-dimethylpropanoate.

(2) Production of 2-chloro-4-(2-2H-1,2,3-triazolyl) methylphenol

A mixture of 2-chloro-4-(2-2H-1,2,3-triazolyl) methylphenyl 2,2-dimethylpropanoate (3 g), 20% aqueous sodium hydroxide solution (10 ml) and ethanol (60 ml) was heated at reflux for 5 hours. The reaction mixture was then concentrated under reduced pressure, to which water was added, and the mixture was adjusted to pH 6.0 with concentrated hydrochloric acid. This mixture was extracted with ethyl acetate. The organic layer was washed with water, dried with anhydrous magnesium sulfate, and concentrated under reduced pressure. The residue was subjected to silica gel column chromatography, which afforded 2-chloro-4-(2-2H-1,2,3-triazolylmethyl)phenol.

According to the same method, 4-(1-pyrazolyl) methylphenol, 4-(2-2H-1,2,3-triazolyl)methylphenol, 2-methyl-4-(2-2H-1,2,3-triazolyl)methylphenol, and 2-methyl-4-(1-pyrazolyl)methylphenol can be obtained.

Intermediate Production Example 3

(1) Production of 2-chloro-4-(2-pyridon-1-yl) methylphenyl 2,2-dimethylpropanoate A mixture of 2-pyridone (3.11 g), sodium hydride (60%, 1.31 g) and anhydrous N,N-dimethylformamide (100 ml) was stirred at 60° to 70° C. under a nitrogen atmosphere for 2 hours. After the evolution of hydrogen gas ceased, the mixture was cooled to 10° C. To this mixture was added dropwise an anhydrous N,N-dimethylformamide (150 ml) solution of 4-bromomethyl-2-chlorophenyl 2,2-dimethylpropanoate (10 g) at room temperature under stirring over 1 hour, and the mixture was stirred at 80° C. for 1 hour. After cooling, the reaction mixture was poured into ice water, which was extracted with ethyl acetate. The organic layer was washed with saturated aqueous ammonium chloride solution and then saturated sodium chloride solution, dried with anhydrous magnesium sulfate, and concentrated under reduced pressure. The residue was subjected to silica gel column chromatography, which afforded 7.60 g of 2-chloro-4-(2-pyridon-1-yl)methylphenyl 2,2-dimethylpropanoate as white crystals. Yield, 73%.

m.p., 145.2° C.

(2) Production of 2-chloro-4-(2-pyridon-1-yl) methylphenol

A mixture of 2-chloro-4-(2-pyridon-1-yl)methylphenyl 2,2-dimethylpropanoate (7.6 g), 20% aqueous sodium hydroxide solution (19 ml) and ethanol (200 ml) was heated at reflux for 5 hours. The reaction mixture was then concentrated under reduced pressure, to which water was added, and the mixture was adjusted to pH 6.0 with concentrated hydrochloric acid. This mixture was extracted with ethyl acetate. The organic layer was washed with water, dried with anhydrous magnesium sulfate, and concentrated under reduced pressure. The residue was subjected to silica gel column chromatography, which afforded 3.98 g of 2-chloro-4-(2-pyridon-1-yl)methylphenol as white crystals. Yield, 71%.

m.p., 193.5° C.

The production examples for the starting compounds used in Production Examples 8 and 9 will be described in the following Reference Production Examples 1 and 2, respectively.

Reference Production Example 1

To a mixture of 4-(1-pyrazolyl)methylphenol (5 g), 1,3-dibromopropane (11.59 g) and water (50 ml) was added dropwise an aqueous solution of sodium hydroxide (1.38 g) dissolved in water (10 ml) while stirring under heating at reflux over 30 minutes. The reaction mixture was then heated at reflux under stirring for further 1 hour, and then cooled to room temperature, which was extracted with diethyl ether (300 ml). The organic layer was washed with 5N aqueous sodium hydroxide solution and then water, dried with anhydrous magnesium sulfate, and concentrated under reduced pressure. The residue was subjected to silica gel chromatography, which afforded 3-[4-(1-pyrazolyl)methylphenoxy]propyl bromide (4.76 g) as white crystals. Yield, 56%.

m.p., 42°–47° C.

Reference Production Example 2

(1) To a mixture of 4-(1-pyrazolyl)methylphenol (15 g), 32.35 g of 1,2-dibromoethane and water (150 ml) was added dropwise an aqueous solution of sodium hydroxide (4.13 g) dissolved in water (30 ml) while stirring under heating at reflux over 30 minutes. The reaction mixture was then heated at reflux under stirring for further 1 hour, and then cooled to room temperature, which was extracted with diethyl ether (300 ml). The organic layer was washed with 5N aqueous sodium hydroxide solution and then water, dried with anhydrous magnesium sulfate, and concentrated under reduced pressure. The residue was subjected to silica gel chromatography, which afforded 2-[4-(1-pyrazolyl)methylphenoxy]ethyl bromide (11.44 g) as white crystals. Yield, 47%.

m.p. 63°–65° C.

(2) A mixture of 2-[4-(1-pyraolyl)methylphenoxy]ethyl bromide (5.0 g), potassium phthalimide (3.95 g) and dry dimethylsulfoxide (50 ml) was heated at 60° C. under stirring for 15 hours. The reaction mixture was then poured into ice water, which was extracted with ethyl acetate. The organic layer was washed with water and then saturated sodium chloride solution, dried with magnesium sulfate, and concentrated under reduced pressure. The crystalline residue was recrystallized from a mixed solvent of ethyl acetate, toluene and ethanol to give 3.0 g of N-{2-[4-(1-pyrazolyl)methylphenoxy]ethyl}-phthalimide as white crystals. Yield, 49%.

m.p., 142°–145° C.

(3) A mixture of N-{2-[4-(1-pyrazolyl)methylphenoxy]ethyl}phthalimide (2.79 g), hydrazine hydrate (0.47 g) and methanol was heated at reflux under stirring for 1 hour. The reaction mixture was then concentrated under reduced pressure to remove most of the methanol, to which methylene chloride (200 ml) was added. The organic layer was washed with 2N sodium hydroxide, dried with anhydrous sodium sulfate, and concentrated under reduced pressure, which afforded 1.69 g of 2-[4-(1-pyrazolyl)methylphenoxy]ethylamine as a colorless oil. Yield, 97%.

$n_D^{23.8}$ 1.5686

The following will describe a production example for the starting compound used in Production Example 10.

Reference Production Example 3

Production of 2-[4-(1-pyrazolyl)methylphenoxy]ethanol

A mixture of 4-(1-pyrazolyl)methylphenol (60 g), ethyl chloroacetate (54.9 g), potassium carbonate (95.1 g) and anhydrous dimethylformamide (500 ml) was heated under stirring at 50° C. for 5 hours, and then cooled to room temperature. The reaction mixture was poured into water (1 liter), which was extracted twice with ethyl acetate (200 ml). The organic layers were combined, washed with water, saturated aqueous ammonium chloride solution, and then saturated sodium chloride, dried with anhydrous magnesium sulfate, and concentrated under reduced pressure, which afforded crude ethyl 4-(1-pyrazolyl)methylpheoxyacetate as an oil.

To an anhydrous tetrahydrofuran (500 ml) suspension of lithium aluminum hydride (38 g) was added dropwise a solution of the above crude ethyl 4-(1-pyrazolyl)methylpheoxyacetate dissolved in anhydrous tetrahydrofuran (100 ml) at –78° C. under stirring over 30 minutes. The mixture was stirred at the same temperature for 1 hour and then at –20° C. for further 2 hours. The reaction mixture was cooled again to –78° C., to which water (38 ml), 15% aqueous sodium hydroxide solution (38 ml) and then water (114 ml) were added dropwise at the same temperature, followed by addition of toluene (500 ml), tetrahydrofuran (500 ml) and then anhydrous sodium sulfate (200 g), and the mixture was stirred at room temperature for 2 hours. The reaction mixture was then filtered through celite, and the filtrate was concentrated under reduced pressure. The residue was subjected to silica gel chromatography, which afforded 64.5 g of 2-[4-(pyrazolyl)methylphenoxy]ethanol as white crystals. Yield, 86% (based upon 4-(1-pyrazolyl)methylphenol)

m.p., 56°–58° C.

The following will describe formulation examples for the harmful-organism controlling agents containing the present compounds as the active ingredients, in which "parts" are by weight and the present compounds are designated by their compound numbers as shown in Tables 15–18.

Formulation Example 1 Emulsifiable concentrates

Ten parts of each of the present compounds 1 to 39 is dissolved in 35 parts of xylene and 35 parts of dimethylformamide, to which 14 parts of polyoxyethylene styryl phenyl ether and 6 parts of calcium dodecylbenzenesulfonate are added, and the mixture is well stirred to give a 10% emulsifiable concentrate of each compound.

Formulation Example 2 Wettable powders

Twenty parts of each of the present compounds 1 to 39 is added to a mixture of 4 parts of sodium lauryl sulfate, 2 parts of calcium lignin sulfonate, 20 parts of synthetic hydrated silicon oxide fine powder and 54 parts of diatomaceous earth, and the mixture is stirred with a juice mixer to give a 20% wettable powder of each compound.

Formulation Example 3 Granules

To 5 parts of each of the present compounds 1 to 39 are added 5 parts of synthetic hydrated silicon oxide fine powder, 5 parts of sodium dodecylbenzenesulfonate, 30 parts of bentonite and 55 parts of clay, and the mixture is well stirred. A suitable amount of water is then added to this mixture, which is further stirred, granulated with a granulator, and air-dried to give a 5% granule of each compound.

Formulation Example 4 Dusts

One part of each of the present compounds 1 to 39 is dissolved in a suitable amount of acetone, to which 5 parts of synthetic hydrated silicon oxide fine powder, 0.3 part of PAP and 93.7 parts of clay are added, and the mixture is stirred with a juice mixer. The removal of acetone by evaporation gives a 1% dust of each compound.

Formulation Example 5 Water-based suspension

Twenty parts of each of the present compounds 1 to 39 and 1.5 parts of sorbitan trioleate are mixed with 28.5 parts of an aqueous solution containing 2 parts of polyvinyl alcohol, and the mixture is pulverized into fine particles (particle size, not more than 3 μm) with a sand grinder, to which 40 parts of an aqueous solution containing 0.05 part of xanthane gum and 0.1 part of aluminum magnesium silicate is added and then 10 parts of propylene glycol is added. The mixture is stirred to give a 20% water-based suspension of each compound.

Formulation Example 6 Oil sprays

First, 0.1 part of each of the present compounds 1 to 39 is dissolved in 5 parts of xylene and 5 parts of trichloroethane. The solution is then mixed with 89.9 parts of deodorized kerosine to give a 0.1% oil spray of each compound.

Formulation Example 7 Oil-based aerosols

First, 0.1 part of each of the present compounds 1 to 39, 0.2 part of tetramethrin, 0.1 part of d-phenothrin, 10 parts of trichloroethane and 59.6 parts of deodorized kerosine are mixed for dissolution. The solution is put in an aerosol vessel, which is then equipped with a valve. Through the said valve, 30 parts of a propellant (liquefied petroleum gas) is charged under increased pressure to give an oil-based aerosol of each compound.

Formulation Example 8 Water-based aerosols

First, 0.2 part of each of the present compounds 1 to 39, 0.2 part of d-allethrin, 0.2 part of d-phenothrin, 5 parts of xylene, 3.4 parts of deodorized kerosine and 1 part of an emulsifier [ATMOS 300 (registered trade name by Arias Chemical Co.)] are mixed for dissolution. The mixture, together with 50 parts of pure water, is put in an aerosol vessel, which is then equipped with a valve. Through the said valve, 40 parts of a propellant (liquefied petroleum gas) is charged under increased pressure to give a water-based aerosol of each compound.

Formulation Example 9 Mosquito-coils

To 0.3 g of each of the present compounds 1 to 39 is added 0.3 g of d-allethrin, and the mixture is dissolved in 20 ml of acetone. The solution is uniformly mixed with 99.4 g of a carrier for mosquito-coils (prepared by mixing Tabu powder, pyrethrum marc powder and wood flour at the ratio of 4:3:3) under stirring, to which 120 ml of water was added. The mixture is well kneaded, molded, and dried to give a mosquito-coil of each compound.

Formulation Example 10 Electric mosquito-mats

To 0.4 g of each of the present compounds 1 to 39, 0.4 g of d-allethrin and 0.4 g of pipenyl butoxide is added acetone for dissolution, so that the total volume comes to 10 ml. This solution in 0.5 ml is uniformly absorbed in a substrate for electric mosquito-mats (prepared by pressing a fibrillated mixture of cotton linter and pulp into a sheet), which is 2.5 cm×1.5 cm and 0.3 cm thick, to give an electric mosquito-mat of each compound.

Formulation Example 11 Heating smoke formulations

First, 100 mg of each of the present compounds 1 to 39 is dissolved in a suitable amount of acetone, and the solution is then absorbed in a porous ceramic plate of 4.0 cm×4.0 cm and 1.2 cm thick to give a heating fumigant of each compound.

Formulation Example 12 Poison baits

First, 10 mg of each of the present compounds 1 to 39 is dissolved in 0.5 ml of acetone, and this solution is added to 5 g of solid bait powder for animals (Breeding Solid Feed Powder CE-2, trade name by Japan Clea Co., Ltd.), which is uniformly mixed. Then, the removal of acetone by air drying gives a 0.5% poison bait of each compound.

The following test examples will demonstrate that the present compounds are useful as the active ingredients of harmful-organism controlling agents, in which the present compounds are designated by their compound numbers as shown in Tables 15 to 18.

Test Example 1 Metamorphosis inhibitory activity against brown rice plant-hopper larvae (foliar treatment)

An emulsifiable concentrate of the test compound obtained according to Formulation Example 1 was diluted with water to a prescribed concentration, and the dilution was sprayed onto rice seedlings cultivated in polyethylene cups at a rate of ml/2 pots. After air drying, ten 3rd-instar larvae of brown rice planthopper (*Nilaparvata lugens*) were freely bred in each cup. After 10 days, the emergence inhibitory rate was determined by the following equation 1:

$$\text{Emergence inhibitory rate}(\%) = \frac{\text{Emergence rate in untreated group} - \text{Emergence rate in treated group}}{\text{Emergence rate in untreated group}} \times 100 \quad [1]$$

The results are shown in Table 19.

TABLE 19

| Test compound | Application concentration (ppm) | Emergence inhibitory rate (%) |
|---|---|---|
| 1 | 0.05 | 100 |
| 2 | 0.05 | 100 |
| 3 | 0.05 | 100 |
| 4 | 0.05 | 100 |
| 5 | 0.05 | 100 |
| 6 | 0.05 | 100 |
| 34 | 0.05 | 100 |

Test Example 2 Metamorphosis inhibitory activity against brown rice plant-hopper larvae (flooding treatment)

An emulsifiable concentrate of the test compound obtained according to Formulation Example 1 was diluted with water to make a prescribed concentration, and the dilution was put into a polyethylene cup of 650 ml volume. After placing thereon a cover with a hole, rice plants cultivated in a polyethylene cup of 30 ml volume were put in the hole so that the bottom was flooded with the chemical solution. After 2 days from the treatment, ten 3rd-instar larvae of brown rice planthopper (*Nilaparvata lugens*) were freely bred in the cup. After 10 days, the emergence inhibitory rate was determined by the above equation 1 (in duplicate). The results are shown in Table 20.

TABLE 20

| Test compound | Application concentration (ppm) | Emergence inhibitory rate (%) |
|---|---|---|
| 2 | 500 | 100 |
| 6 | 500 | 100 |
| 7 | 500 | 100 |
| 34 | 500 | 100 |

Test Example 3 Emergence inhibitory activity against common mosquito

An emulsifiable concentrate of the test compound obtained according to Formulation Example 1 was diluted with water, and this dilution in 0.7 ml was added to 100 ml of ion-exchanged water (concentration of active ingredient, 3.5 ppm). Twenty last instar larvae of common mosquito (*Culex pipiens pallens*) were set free therein, and bred while giving bait for 8 days. The emergence inhibitory rate was determined by the above equation 1. The results are shown in Table 21.

TABLE 21

| Test compound | Emergence inhibitory rate (%) |
|---|---|
| 3 | 100 |
| 12 | 100 |
| 13 | 100 |
| 14 | 100 |
| 31 | 100 |
| 32 | 100 |
| 33 | 100 |

Test Example 4 Insecticidal test against cotton aphid (*Aphis gossypii*)

An emulsifiable concentrate of the test compound obtained according to Formulation Example 1 was diluted with water to a prescribed concentration, and the dilution was poured upon the pans near the roots of cucumbers cultivated in polyethylene cups for flooding at a rate of 100 cc/1 pot. After 3 days from the treatment, five adults of aphid were freely bred on the main leaves. After 14 days from the free breeding, the control value was determined by the following equation 2:

$$\text{Control value (\%)} = \left(1 - \frac{C_b \cdot T_{ai}}{T_b \cdot C_{ai}}\right) \times 100 \qquad [2]$$

where $C_b$ is the number of insects before the treatment in the untreated group; $C_{ai}$, the number of insects during the observation in the untreated group; $T_b$, the number of insects before the treatment in the experimental group; and $T_{ai}$, the number of insects during the observation in the experimental group.

The results are shown in Table 22.

TABLE 22

| Test compound | Application concentration (ppm) | Control value (%) |
|---|---|---|
| 1 | 500 | 94 |
| 3 | 500 | 96 |
| 14 | 500 | 98 |
| 15 | 500 | 83 |

Industrial Applicability

According to the present invention, there are provided novel ether compounds having excellent controlling effects against harmful organisms. These ether compounds are useful as the active ingredients of harmful-organism controlling agents.

We claim:

1. An ether compound of the general formula:

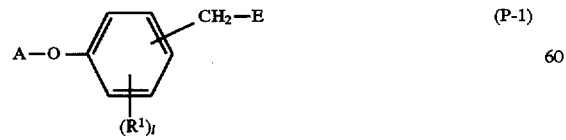
(P-1)

wherein $R^1$ is halogen;

A is any of the groups of the following formulas Q-1 to Q-11:

A is any of the groups of the following general formulas Q-1 to Q-11:

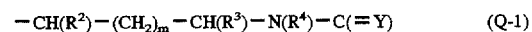 (Q-1)

 (Q-2)

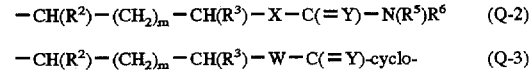 (Q-3)

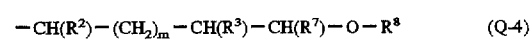 (Q-4)

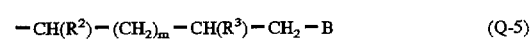 (Q-5)

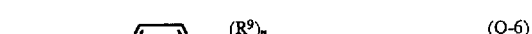 (Q-6)

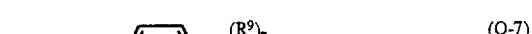 (Q-7)

 (Q-8)

 (Q-9)

 (Q-10)

 (Q-11)

$R^2$, $R^3$, $R^4$ and $R^7$ are independently hydrogen or methyl;

$R^5$ and $R^8$ are independently $C_1$–$C_4$ alkyl (optionally substituted with halogen or methoxy), $C_3$–$C_4$ alkenyl (optionally substituted with halogen) or $C_3$–$C_4$ alkynyl (optionally substituted with halogen);

$R^6$ is a group represented by $R^5$, or hydrogen;

$R^9$ is halogen or $C_1$–$C_4$ alkyl (optionally substituted with halogen);

$R^{10}$ and $R^{11}$ are independently hydrogen, $C_1$–$C_4$ alkyl or $C_3$–$C_4$ alkenyl;

B is a group of the general formula:

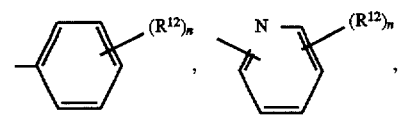

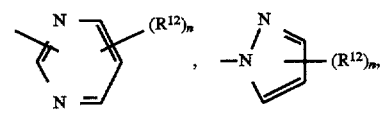

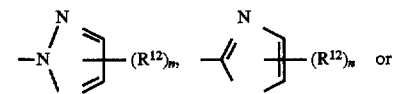

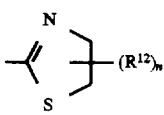

E is a group of the general formula:

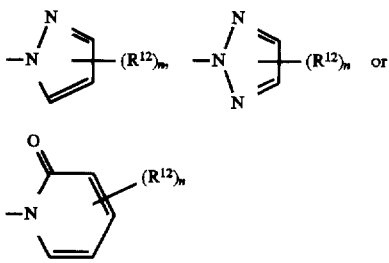

$R^{12}$ is halogen, or methyl optionally substituted with halogen;
X and Y are independently oxygen or sulfur;
W is oxygen, sulfur or NH; and
l, m and n are independently an integer of 0 to 2.

2. An ether compound according to claim 1, wherein E is a group of the general formula:

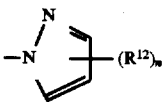

(P-3)

wherein $R^{12}$ and n are as defined above.

3. An ether compound according to claim 2, wherein n is 0.

4. An ether compound according to claim 1, wherein A is a group represented by Q-1, Q-2, Q-3, Q-5 or Q-10.

5. An ether compound according to claim 1, wherein A is a group represented by Q-1, Q-2, Q-3, Q-5 or Q-10; $R^2$, $R^3$ and $R^4$ are all hydrogen; and m is 0.

6. 2-[4-(1-Pyrazolyl)methylphenoxy]ethylcarbamic acid methyl ester.

7. 1-{3-[4-(1-Pyrazolyl)methylphenoxy]propyl}pyrazole.

8. N-{2-[4-(1-Pyrazolyl)methylphenoxy]ethyl}cyclopropanecarboxide.

9. 4-[4-(1-Pyrazolyl)methylphenoxy]methyl-2-ethyl-1,3-dioxolane.

10. A harmful-organism controlling agent characterized by comprising as an active ingredient an ether compound according to claim 1.

11. An phenol compound of the general formula:

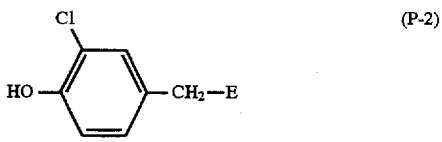

(P-2)

wherein E is a group of the general formula:

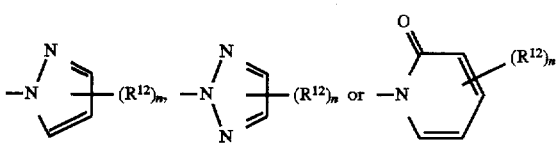

$R^{12}$ is halogen, or methyl optionally substituted with halogen; and n is an integer of 0 to 2.

* * * * *